United States Patent [19]
Hayashi et al.

[11] Patent Number: 5,675,085
[45] Date of Patent: Oct. 7, 1997

[54] METHOD AND APPARATUS FOR MEASURING DEPTH OF CRACK FOR REINFORCED CONCRETE CONSTRUCTION

[75] Inventors: Masano Hayashi; Masatoshi Kimura; Kaoru Motegi, all of Tokyo; Jiro Tsuchikawa, Kawaguchi; Masayuki Hirose; Koudo Taya, both of Tokyo, all of Japan

[73] Assignees: H & B System Inc.; Imperial Consultant Inc., both of Tokyo, Japan

[21] Appl. No.: 548,955

[22] Filed: Oct. 27, 1995

[30] Foreign Application Priority Data

Oct. 28, 1994 [JP] Japan ................................ 6-265885
Dec. 13, 1994 [JP] Japan ................................ 6-309322

[51] Int. Cl.$^6$ ................................................ G01N 29/04
[52] U.S. Cl. ........................ 73/628; 73/602; 73/597; 73/624
[58] Field of Search ........................ 73/628, 627, 597, 73/598, 602, 618, 624, 625

[56] References Cited

U.S. PATENT DOCUMENTS

| | | | |
|---|---|---|---|
| 3,592,052 | 7/1971 | Giacomo et al. | 73/596 |
| 4,052,889 | 10/1977 | Mucciarda et al. | 73/602 |
| 4,522,064 | 6/1985 | McMillan | 73/628 |
| 4,570,487 | 2/1986 | Gruber | 73/628 |
| 4,640,132 | 2/1987 | Flora et al. | 73/602 |
| 4,658,649 | 4/1987 | Brook | 73/624 |
| 4,953,405 | 9/1990 | Hara et al. | 73/602 |
| 5,431,053 | 7/1995 | Fink | 73/596 |
| 5,492,012 | 2/1996 | Terhune | 73/596 |

Primary Examiner—Hezron E. Williams
Assistant Examiner—Helen C. Kwok
Attorney, Agent, or Firm—Oblon, Spivak, McClelland, Maier & Neustadt, P.C.

[57] ABSTRACT

By arranging a pair of an ultrasonic wave transmitting sensor and an ultrasonic wave receiving sensor in opposition across a crack in a reinforced concrete construction. An ultrasonic wave is transmitted from the ultrasonic wave transmitting sensor at a first position. A reflected wave is then received by the ultrasonic wave receiving sensor at the first position. Also, the ultrasonic wave is transmitted from the ultrasonic wave transmitting sensor at a second position. A reflected wave is then received by the ultrasonic wave receiving sensor at the second position. The received waves at two positions are provided mutual phase shift for a predetermined period and summed in reversed phase for deriving a rise time of the wave reflected from the crack. By this, even when reinforcement is arranged in the concrete, the noise component superimposed on the received wave due to presence of the reinforcement can be eliminated to permit high precision measurement of the depth of the crack irrespective of the presence of the reinforcement at high density.

7 Claims, 20 Drawing Sheets

FIG. 1 (PRIOR ART)
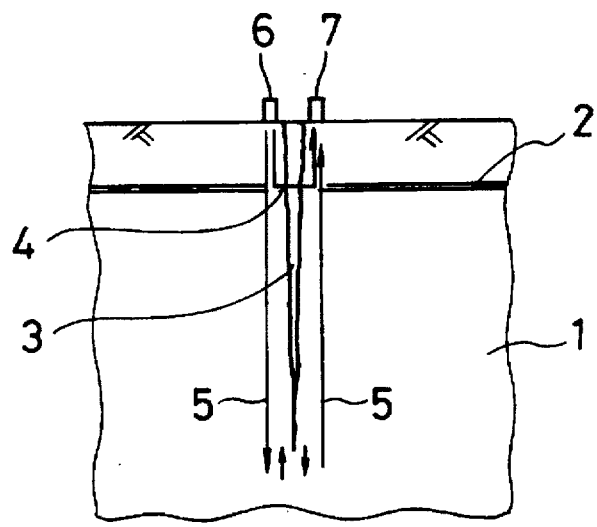
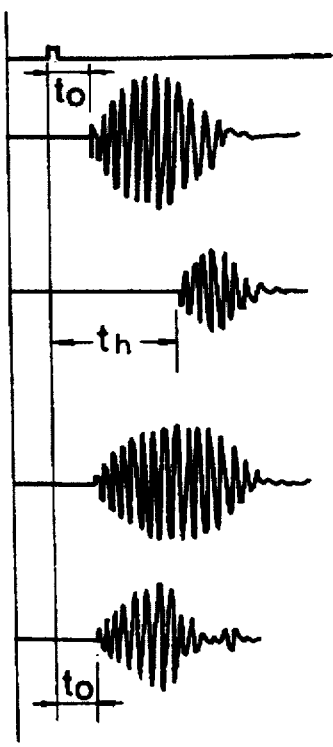
FIG. 2A (PRIOR ART)
FIG. 2B (PRIOR ART)
FIG. 2C (PRIOR ART)
FIG. 2D (PRIOR ART)

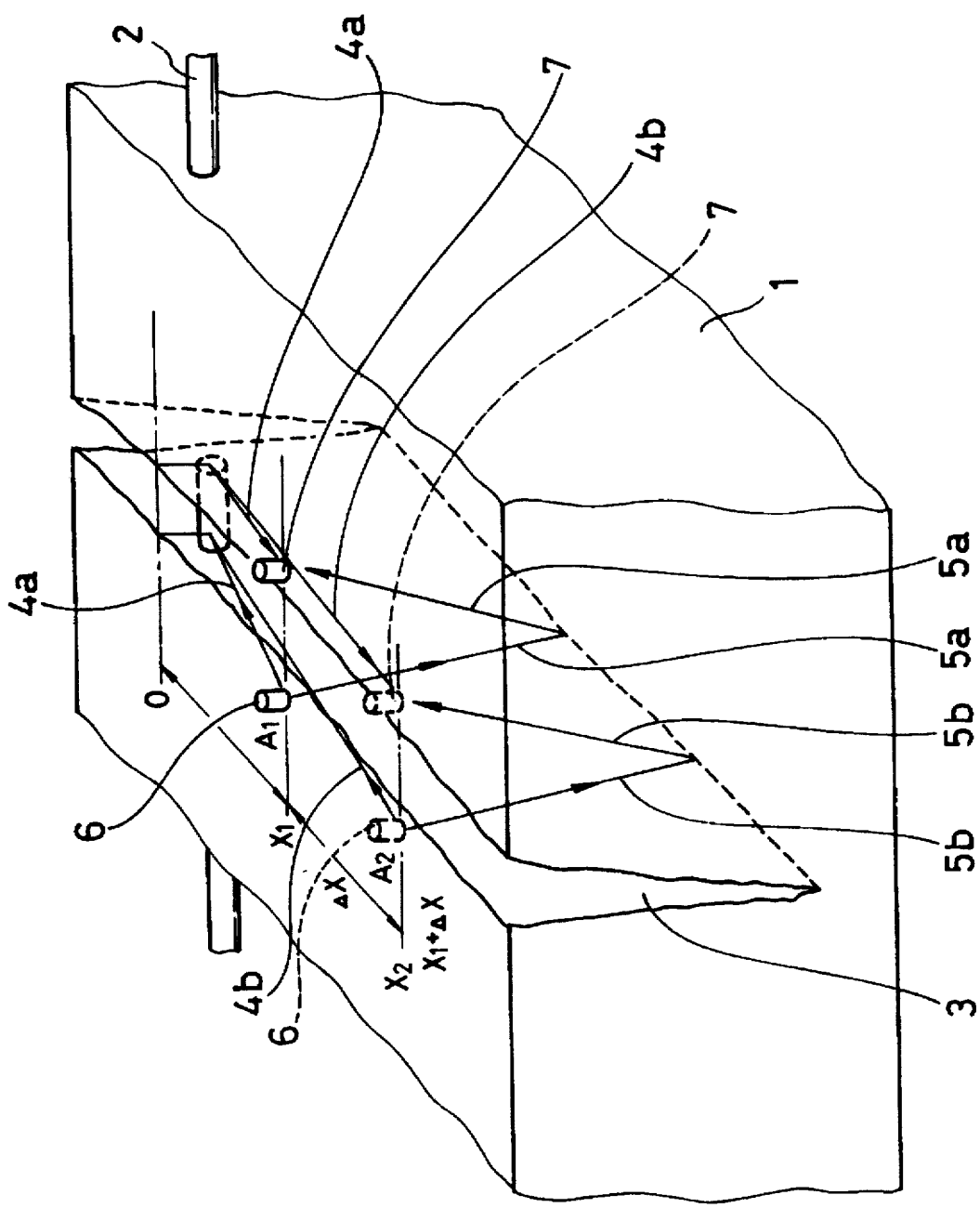

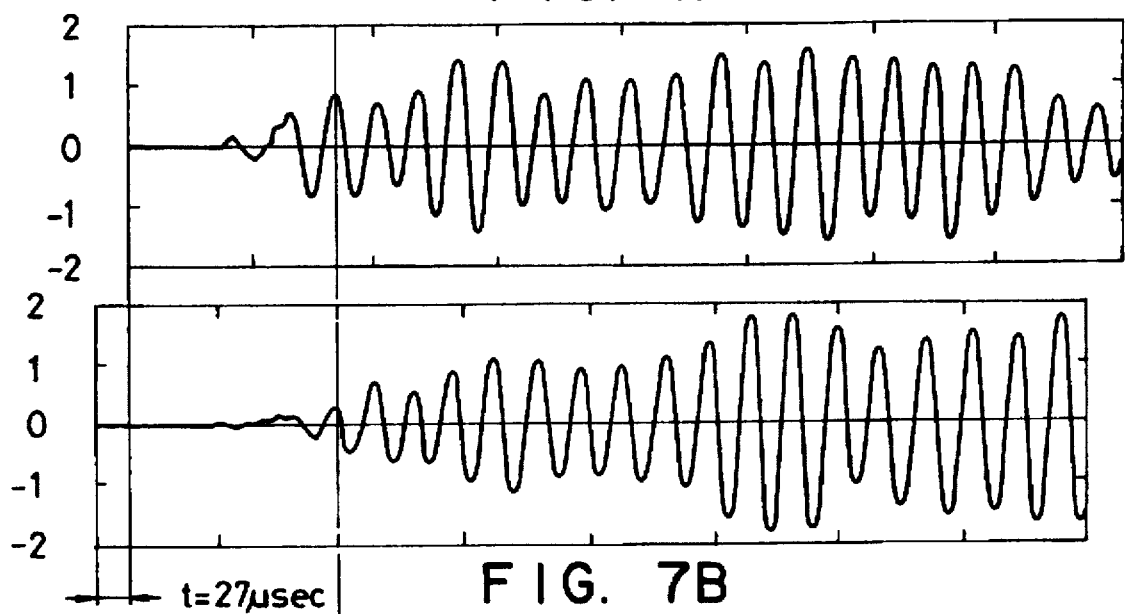
FIG. 7A
FIG. 7B
t=27μsec
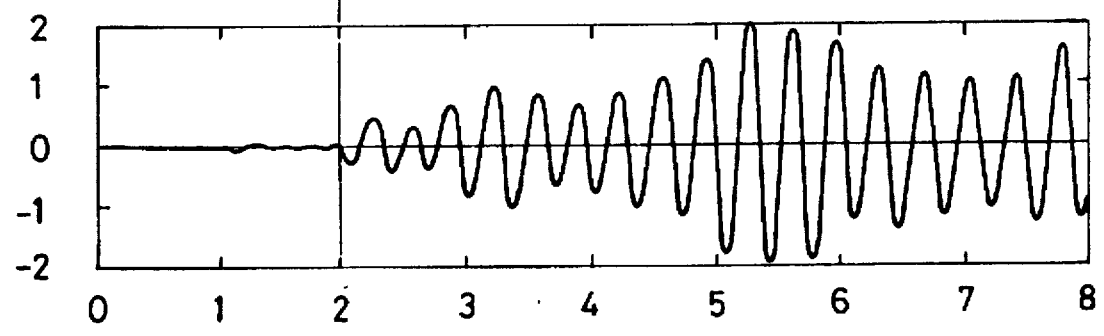
FIG. 7C

FIG. 8A
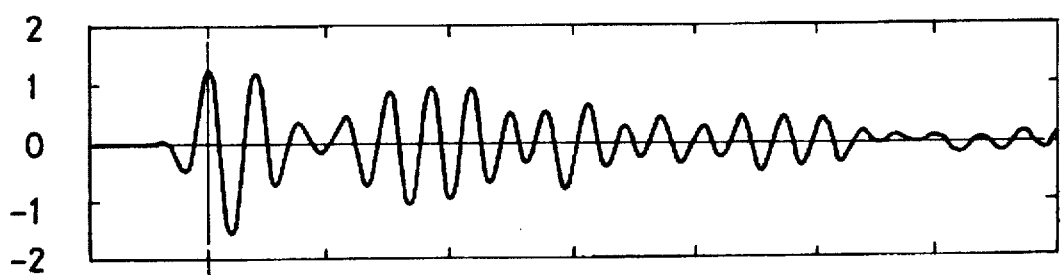
FIG. 8B
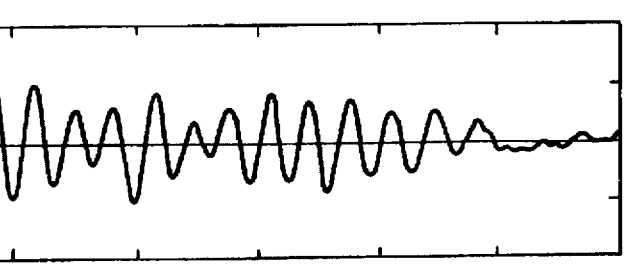
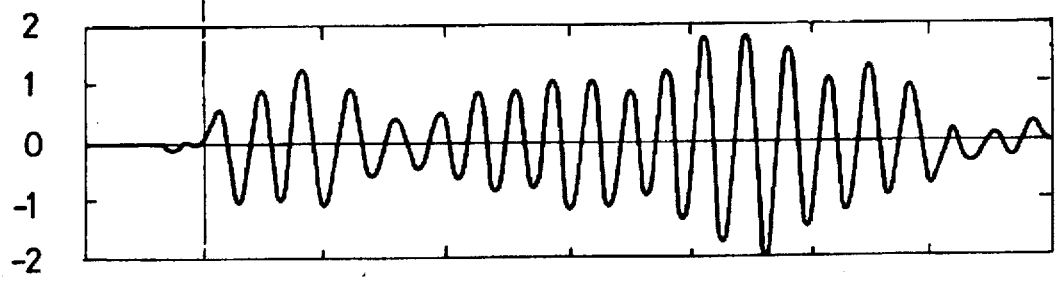
FIG. 8C

FIG. 22
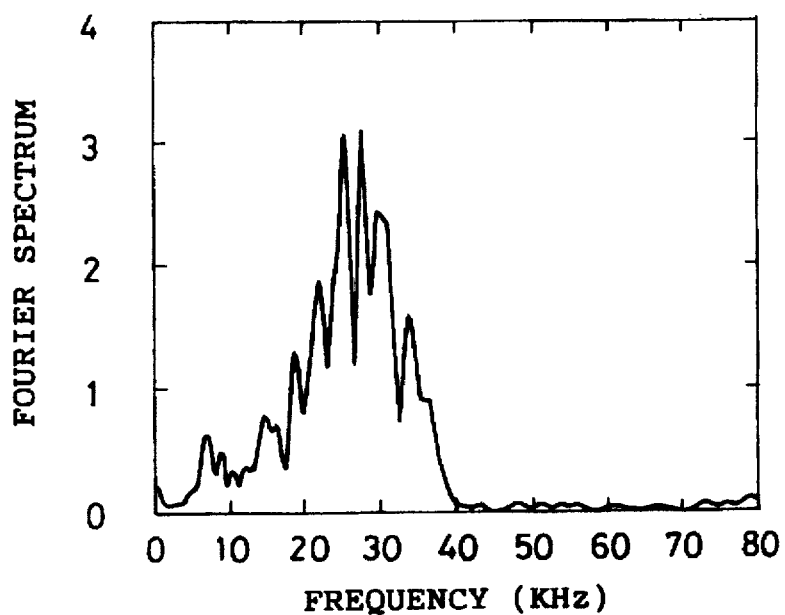
FIG. 23A
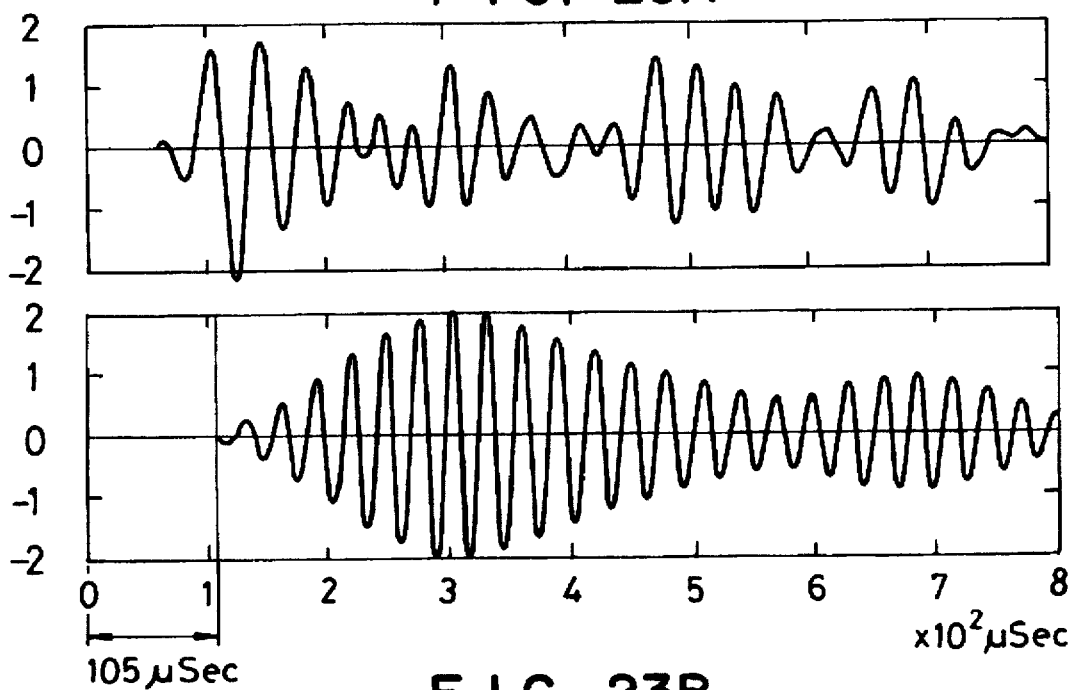
FIG. 23B

METHOD AND APPARATUS FOR MEASURING DEPTH OF CRACK FOR REINFORCED CONCRETE CONSTRUCTION

BACKGROUND OF THE INVENTION

1. Field of the Invention

The present invention relates to a method and apparatus for measuring depth of crack in a reinforced concrete construction, in which reinforcements(reinforcing bars) are arranged in a given pitch buried in a concrete.

2. Description of the Related Art

A measure for fatigue is an important problem for reinforced concrete construction, such as buildings, tunnels, underground walls, road construction and so forth due to inherent secular variation and repeated loading of external disturbance. For the measure of fatigue, it becomes necessary to measure the depth of crack of the concrete with high precision.

As the conventional crack measuring method, there is a short distance detouring wave method. The crack measuring method employing this short distance detouring wave method is illustrated in FIG. 1. As shown in FIG. 1, reinforcements 2 are buried in the concrete 1. When the crack 3 is caused from the surface of the concrete, an ultrasonic wave transmitting sensor 6 and an ultrasonic wave receiving sensor 7 are arranged at both sides of the crack 3. The ultrasonic wave transmitting sensor 6 then transmits an ultrasonic wave toward the inside of the concrete 1. Then, the ultrasonic wave propagates through a path 5. The ultrasonic wave is reflected from the deepest portion of the crack 3. The reflected ultrasonic wave passes the same path 5 and is received by the ultrasonic wave receiving sensor 7.

The received wave is shown in FIG. 2B. On the basis of a time difference $t_h$ from transmission of the ultrasonic wave to reception of the reflected wave by the ultrasonic wave receiving sensor 7, and a sonic speed ($C_s$m/sec.) of the concrete which is obtained through experiments, the depth of the crack d can be obtained through the following equation:

$$d = C_s \times t_h / 2 \quad (1)$$

Accordingly, by measuring $t_h$, the depth d of the crack can be derived.

However, in the concrete construction, in which reinforcement is provided in high density, an ultrasonic wave incident to the ultrasonic wave receiving sensor 7 via the reinforcement 2 is present as shown by a path 4 in FIG. 1. The waveform of such ultrasonic wave reflected from the reinforcement is, as shown in FIG. 2A, detected at a timing $t_0$ from transmission of the ultrasonic wave. Thus, the ultrasonic wave reflected from the reinforcement can be detected at earlier timing than the detection timing of the ultrasonic wave reflected from the bottom of the crack as illustrated in FIG. 2B.

Therefore, a reception wave from the reinforcement 2 extending through the crack via the path 4 (FIG. 2A) and a reception wave from the deepest portion of the crack via the path 5 (FIG. 2B) are input to the ultrasonic wave receiving sensor 7 as a wave having a waveform, in which both reception waves are superimposed to each other. Typical reception waves input to the ultrasonic wave receiving sensor 7 are shown in FIGS. 2C and 2D. Such reception wave are detected at a timing $t_0$ from transmission of the ultrasonic wave, and the reception timing of the leading end of the ultrasonic wave reflected from the deepest portion of the crack 3 can become not perceptible due to presence of the reflected wave from the reinforcement.

As a method for measuring the depth of the crack depth in the reinforced construction, other than the short distance detouring method, a propagation time method, BS method, lamp method, SH (lateral wave) method, spectroscopy method and so forth are available. However, such methods are also only applicable for the non-reinforced concrete or the reinforced concrete having reinforcement set in low density, similarly to the short distance detour method. Therefore, none of the methods is applicable for detection of the depth of the crack in the reinforced concrete having high density reinforcement.

On the other hand, with the low density of reinforcement, it becomes possible to measure the depth of the crack by arranging the ultrasonic wave transmitting sensor 6 and the ultrasonic wave receiving sensor 7 away from the reinforcement so that the ultrasonic wave reflected at the deepest portion of the crack may reach the ultrasonic wave receiving sensor 7 at earlier timing than the ultrasonic wave reflected from the reinforcement.

However, this method encounters a difficulty in that since the depth of the crack per se is not yet known, it is uncertain whether the distance between the reinforcement and the crack is shorter than the depth of the crack or not. Namely, even when the sensors are nominally arranged at positions sufficiently distant from the reinforcement, it is still possible that the depth of the crack is greater than the distance to the reinforcement. If this is the case, erroneous detection can be caused. Therefore, this method is still not reliable. Therefore, in the conventional method, the crack depth can be accurately measured only in the case where the concrete is non-reinforced concrete.

SUMMARY OF THE INVENTION

It is an object of the present invention to provide a method and apparatus for measuring the depth of the crack of a reinforced concrete construction, which permits detection of crack in the concrete at high precision even when the reinforcement is arranged in the concrete at high density.

In the present invention, an ultrasonic wave transmitting sensor and an ultrasonic wave receiving sensor are employed for transmitting an ultrasonic wave at two positions along a crack, and receives reflected waves at respective positions. The waves received at a first position and a second position are provided mutual phase shift for a predetermined period, and summed in the reversed phase. The predetermined period is determined depending upon relative distance between the transmitting position and the receiving position of the ultrasonic wave. Thus, among the waves received by the ultrasonic wave receiving sensor at respective positions, the noise component reflected by reinforcement can be canceled by providing the phase shift and summing in reversed phase. At this time, since substantially the same depth of the crack is detected at the first and second positions, the component of the wave reflecting the depth of the crack cannot be cancelled by phase shifting and summing in reversed phase. Therefore, after the foregoing process, only a component of the wave reflected from the deepest portion of the crack remains to permit detection of the depth of the crack at high precision.

It should be noted that transmission and reception of the ultrasonic wave can be done by shifting a pair of the ultrasonic wave transmitting sensor and the ultrasonic wave receiving sensor, or in the alternative, by providing a plurality of pairs of ultrasonic wave transmitting sensors and the ultrasonic wave receiving sensors at respective positions.

Through analysis of over 600 of ultrasonic waves transmitted from the ultrasonic wave transmitting sensor and received by the ultrasonic wave receiving sensor, the inventors have found that the ultrasonic wave reflected by the reinforcement and the ultrasonic wave reflected by the bottom of the crack are distinct in the following respects.

Namely, in the vicinity of predominant oscillation frequency (the oscillation frequency at which the peak is dominant) in the input ultrasonic wave, Fourier spectrums of the basic oscillation frequencies of the reflected wave from the bottom of the crack, the reflected wave from the reinforcement and the waves received from other routes and their high degree oscillation frequency are dominant. Thus large number of spectrums are concentrated in the vicinity of predominant oscillation frequency. These Fourier spectrums have the following nature.

The spectrum value of the dominant oscillation frequency of the wave from the crack is held substantially unchanged when the measuring points are shifted along the crack.

On the other hand, since the reinforcements are present at shallow position in the vicinity of the surface of the reinforced concrete, even by small distance of shift of the measuring point, substantial magnitude of variation is caused in the relative position between the measuring point and the reinforcement. Therefore, the dominant oscillation frequency and the spectrum value of the reflected wave from the reinforcement may be varied significantly by shifting of the measuring point. Also, greater distance between the measuring point and the reinforcement results smaller spectrum value of the reflected wave from the reinforcement. Therefore, the reflected wave from the crack and the reflected wave from the reinforcement are clearly discriminated in the spectrum.

On the other hand, the waves from other routes, such as the wave from the bottom of the concrete or so forth are received at later timing than the reflected wave from the crack, and thus cannot be a problem.

As a result of finding of such phenomenon, the inventors have found a method for deriving the depth of the crack by utilizing high speed Fourier transformation and inverse transformation. Namely, an pair of ultrasonic wave transmitting sensor and an ultrasonic wave receiving sensor are arranged in opposition across the crack. The ultrasonic wave is transmitted from the ultrasonic wave transmitting sensor and the reflected wave is received by the ultrasonic wave receiving sensor. For the received wave, Fourier transformation is performed. In the Fourier spectrum thus obtained, there are present the frequency in which the spectrum value varies significantly depending upon the position of the ultrasonic wave receiving sensor, namely the measuring position, and the frequency in which the spectrum value is relatively constant and does not be varied significantly. Therefore, selecting the frequency range where the spectrum value is held substantially unchanged, inverse Fourier transformation is performed. Thus, the component of the wave from the reinforcement can be reduced or eliminated to obtain a time sequence wave which contains a large fraction of the component of the wave from the crack.

With respect to the time sequence wave thus obtained, Fourier transformation and inverse Fourier transformation are repeated for a plurality of times to cause convergence. Then, the time sequence wave consisted of the only wave component reflected from the crack can be obtained. By this, the wave component reflected from the reinforcement can be removed from the original waveform so as to permit detection of the rise time of the wave from the crack. Thus, the depth of the crack can be measured at high precision.

As set forth above, according to the present invention, by employing a pair of the ultrasonic wave transmitting sensor and the ultrasonic wave receiving sensor, the depth of the crack can be detected at high precision easily with relatively simple apparatus. Furthermore, since influence of the reinforcement can be avoided, precision in detection of the crack depth can be significantly improved. Thus, the present invention should contribute in inspection of the fatigue condition of the reinforced concrete constructions.

BRIEF DESCRIPTION OF THE DRAWINGS

The present invention will be understood more fully from the detailed description given herebelow and from the accompanying drawings of the preferred embodiment of the invention, which, however, should not be taken to be limitative to the present invention, but are for explanation and understanding only.

In the drawings:

FIG. 1 is an illustration showing a conventional measuring method the crack depth employ a short distance detouring method;

FIGS. 2A to 2D are illustrations showing reception waves in the method illustrated in FIG. 1;

FIG. 3 is a perspective view showing the preferred embodiment of a crack depth measuring apparatus according to the present invention;

FIGS. 7A, 7B and 7C are illustrations showing reception waves obtained from the model of FIG. 5;

FIGS. 8A, 8B and 8C are illustrations showing reception waves obtained from the model of FIG. 6;

FIG. 22 is a graph showing a Fourier spectrum of C30 reception wave;

FIGS. 23A and 23B are graphs showing the original wave and the converging wave of a C30 reception wave, respectively;

DESCRIPTION OF THE PREFERRED EMBODIMENT

Figure 4A:
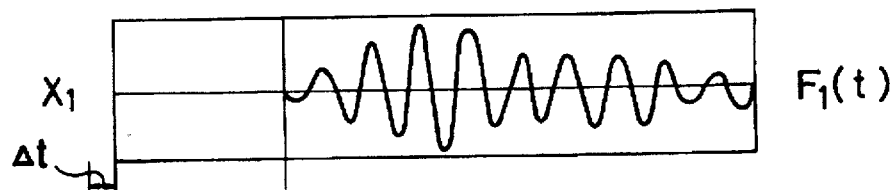
FIGS. 4A, 4B and 4C are illustrations showing reception waves in the preferred embodiment.

The preferred embodiment of the present invention will be discussed hereinafter in detail with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to unnecessary obscure the present invention.

FIG. 3 is a perspective view showing the preferred embodiment of a crack depth measuring apparatus for implementing the preferred embodiment of the crack depth measuring method according to the invention. As shown in FIG. 3, reinforcements 2 are buried in a concrete 1. When crack 3 is caused, in the shown embodiment, an ultrasonic wave transmitting sensor 6 and an ultrasonic wave receiving sensor 7 are arranged in opposition to each other across the crack 3. Then, ultrasonic waves are transmitted to two positions $A_1$ and $A_2$ along the crack, and receiving reflected ultrasonic wave.

It should be noted that as seen in the plan view, a distance between the reinforcement 2 and the ultrasonic wave transmitting sensor 6 and the ultrasonic wave receiving sensor 7 arranged at a first position $A_1$ is assumed to be $X_1$, a distance between the reinforcement 2 and the ultrasonic wave transmitting sensor 6 and the ultrasonic wave receiving sensor 7 arranged at a second position $A_2$ is assumed to be $X_2$, and a difference between $X_1$ and $X_2$ is assumed as $\Delta X$.

In the shown embodiment, after arranging respective sensors at a first position $A_1$, the ultrasonic wave is transmitted from the ultrasonic wave transmitting sensor 6. Then, the ultrasonic wave transmitted from the ultrasonic wave transmitting sensor 6 reaches the reinforcement 2 via a path $4a$ and then reflected toward the ultrasonic wave receiving sensor 7 via the path $4a$ to be detected. On the other hand, the ultrasonic wave also reaches the deepest portion of the crack 3 via a path $5a$ and reflected toward the ultrasonic wave receiving sensor 7 via the path $5a$.

Next, the ultrasonic wave transmitting sensor 6 and the ultrasonic wave receiving sensor 7 are arranged at a second position $A_2$. Then, the ultrasonic wave transmitted from the ultrasonic wave transmitting sensor 6 reaches the reinforcement 2 via a path $4b$ and then reflected toward the ultrasonic wave receiving sensor 7 via the path $4b$ to be detected. On the other hand, the ultrasonic wave also reaches the deepest portion of the crack 3 via a path $5b$ and reflected toward the ultrasonic wave receiving sensor 7 via the path $5b$.

Figure 4B:
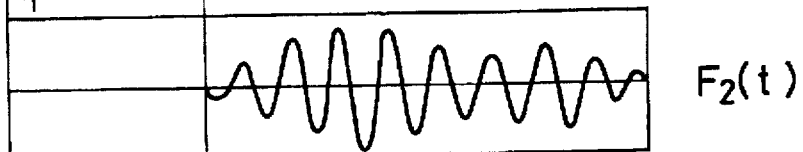
Figure 4C:
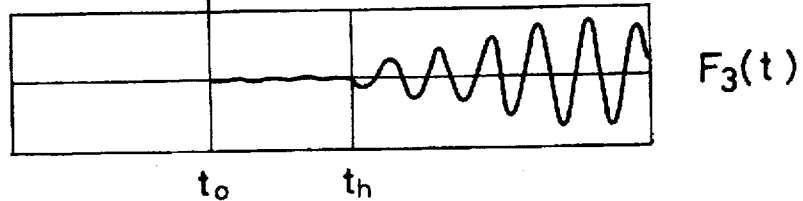

Waveforms of reception waves of the ultrasonic wave receiving sensor 7 at the foregoing two positions are shown in FIGS. 4A to 4C. FIG. 4A is the reception wave ($F_1(t)$), in which the ultrasonic wave transmitted from the ultrasonic wave transmitting sensor 6 is received by the ultrasonic wave receiving sensor 7 at the first position $A_1$. On the other hand, FIG. 4B is the reception wave ($F_2(t)$), in which the ultrasonic wave transmitted from the ultrasonic wave transmitting sensor 6 is received by the ultrasonic wave receiving sensor 7 at the second position $A_2$. It should be noted that both reception waves have mutual phase shift in the extent of $\Delta t$. The $\Delta t$ is determined depending upon the distance $\Delta X$ between the first position $A_1$ and the second position $A_2$.

Both reception waves of FIGS. 4A and 4B include the ultrasonic wave reflected from the reinforcement and the ultrasonic wave reflected from the deepest portion of the crack. Even by observing these reception waves, it is not possible to identify the leading end of the reception wave from the bottom of the crack. However, as shown in the following equation, by providing a mutual phase shift in the extent of $\Delta t$ for both reception waves and by summing them in reversed phase, the ultrasonic wave component reflected from the reinforcement can be canceled. Thus, only ultrasonic wave reflected from the deepest portion, i.e. bottom of the crack can be detected.

$$F_3(t) = -\alpha F_1(t - \Delta t) + F_2(t) = -\alpha f_1(t - \Delta t) + f_2(t) - \alpha f_h(t - \Delta t) + \quad (2)$$

$$f_h(t) = -\alpha f_h(t - \Delta t) + f_h(t)$$

wherein $F_1(t) = f_1(t) + f_h(t)$ $F_2(t) = f_2(t) + f_h(t)$ $f_1(t)$ is a waveform of the ultrasonic wave transmitted from the ultrasonic wave transmitting sensor 6 and reflected from the reinforcement at the first position $A_1$, $f_2(t)$ is a waveform of the ultrasonic wave transmitted from the ultrasonic wave transmitting sensor 6 and reflected from the reinforcement at the second position $A_2$, $f_h(t)$ is a waveform of the ultrasonic wave transmission from the ultrasonic wave transmitting sensor 6 at the first position $A_1$ and the second position $A_2$ and reflected from the deepest portion of the crack.

In establishment of the foregoing first equation (2), the following assumptions are taken. Namely, when $\Delta X$ is small, the ultrasonic wave transmitted from the ultrasonic wave transmitting sensor 6 and reflected by the reinforcement, it should have the same period and relative amplitude at the foregoing two positions. In other words, the absolute amount of the amplitude is greater at the ultrasonic wave at the position close to the reinforcement than that of the remote reinforcement, at both positions. However, in terms of the relative amplitude, they becomes equal. Also, the wave shape of both are the same. However, in case of the ultrasonic wave reflected from the bottom of the crack should have the same rising timing $T_h$ regarding the depth of the crack is not changed at the two positions.

Accordingly, the foregoing equation (2) represents that the reception wave of FIG. 4A is shifted in the extent of $\Delta t$ and is multiplied for a times in order to correct the magnitude of the absolute amplitude to establish $\alpha F_1(t - \Delta t)$, then $-F_1(t - \Delta t)$ obtained by reversing the phase of $\alpha F_1(t - \Delta t)$ is summed with the reception signal $F_2(t)$ of FIG. 4B. The later part of the foregoing equation show respective reception wave separating into the wave from the reinforcement and the wave from the crack. Based on the assumption, since the ultrasonic wave reflected from the reinforcement, relative amplitude and the period are the same, $-\alpha F_1(t-\Delta t)+f_2(t)$ becomes 0. Therefore, from the second equation, third equation can be established. In the third equation, only the ultrasonic wave reflected from the deepest portion of the crack appears. This is shown in FIG. 4C. FIG. 4C shows the waveform of the ultrasonic wave reflected from the deepest portion of the crack as expressed by $F_3(t)=-\alpha f_h(t-\Delta t)+f_h(t)$. The leading point is the timing $t_h$. Therefore, on the basis of the time $t_h$, the depth of the crack can be detected.

In practice, a time difference $\Delta t$ for making $-\alpha f_1(t-\Delta t)+f_2(t)$ to be a value as close as possible to 0, can be derived by shifting the measured reception waves on the time axis, a position where both terms are mutually canceled or become satisfactorily small.

For instance, assuming $X_1=0$ and $\Delta X=10$ mm, and the position of the reinforcement from the surface of the concrete is 50 mm, a transmission distanced $d_1$ of the ultrasonic wave reflected from the reinforcement at the position $d_1$ becomes $50\times2=100$ mm, at the first position $A_1$. On the other hand, the transmission distanced $d_2$ of the ultrasonic wave reflected from the reinforce at the position $d_1$ becomes $2\times(10^2+50^2)^{1/2}=102$ mm at the second position $A_2$. The phase difference $\Delta t$ is assuming that the sonic speed of the concrete is 4.2 mm/μsec., $\Delta t=(102-100)/4.2=0.48$ to 0.5 μsec. Accordingly, by providing the time difference in such extent for both reception wave and by overlapping them in the reversed phase, the component of the wave reflected from the reinforcement can be canceled.

Figure 5:
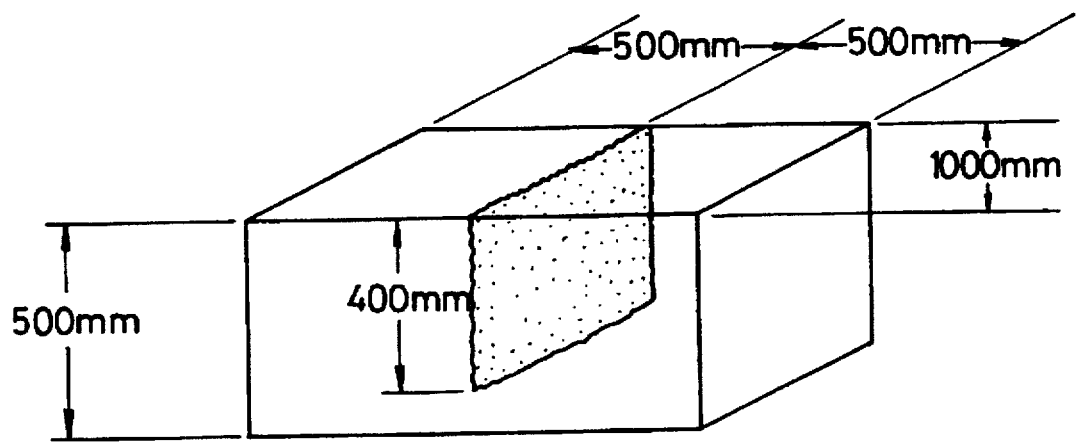
FIG. 5 is an illustration showing a model for demonstrating the effect of the invention.
Figure 6:
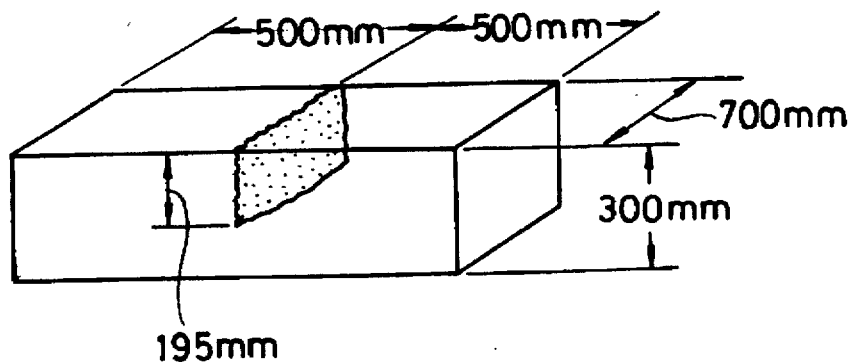
FIG. 6 is an illustration of another model.

Next, discussion will be given for the result of actual measurement of the depth of the crack according to the present invention. FIGS. 5 and 6 are models of the reinforced concrete and crack prepared for measurement test. The model shown in FIG. 5 has a crack in the depth of 400 mm. On the other hand, the model of FIG. 6 has a crack in the depth of 195 mm. Then, for these models, the sensors are located at various distances from the reinforcement for receiving the reception waves. As a results of analysis of the reception wave detected by the reception sensor, the reception waveform shown in FIG. 7 is obtained with respect to the model of FIG. 5 and the reception waveform shown in FIG. 8 is obtained with respect to the model of FIG. 6. Thus, the rising timing $t_h$ of the ultrasonic wave reflected from the bottom of the crack was measured.

Figure 9:
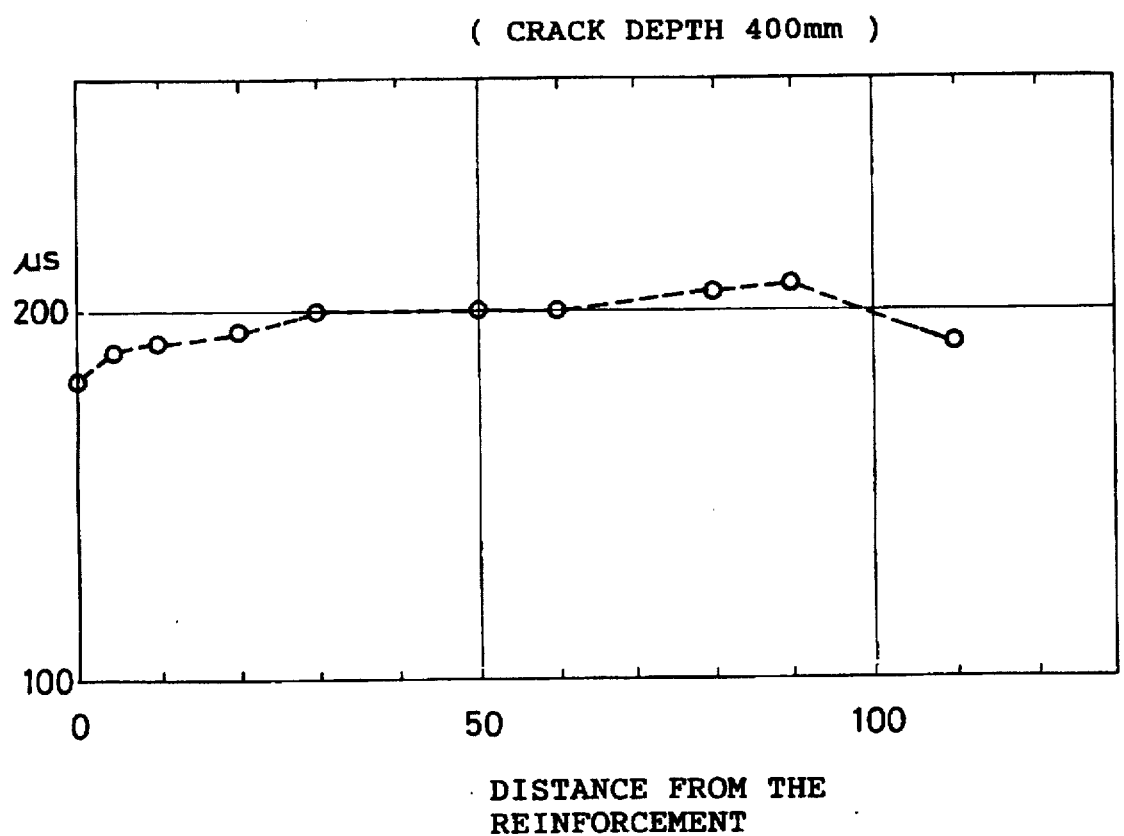
FIG. 9 is a graph showing actually measured values of the crack depth in the case of the model of FIG. 5, in relation to the distance from the reinforcement.
Figure 10:
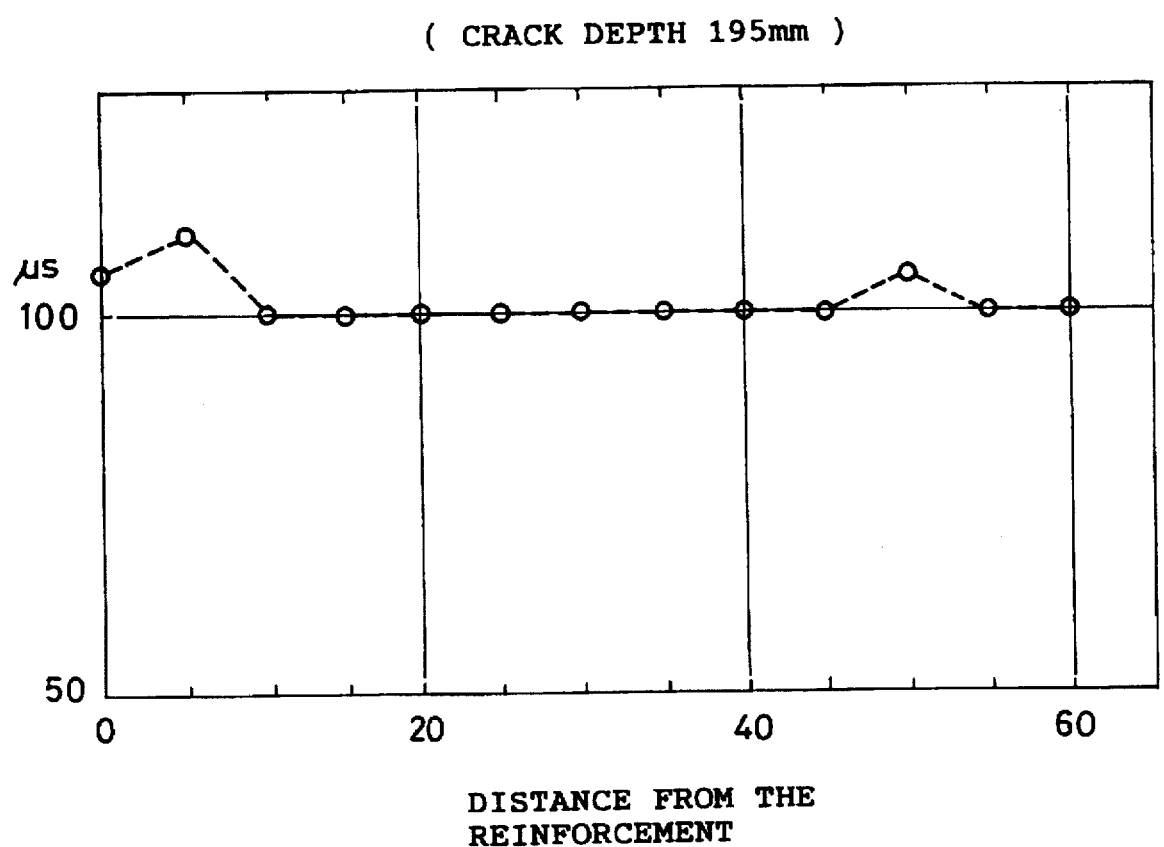
FIG. 10 is a graph showing actually measured values of the crack depth in the case of the model of FIG. 6, in relation to the distance from the reinforcement.

FIGS. 9 and 10 are plots of the rising timing $t_h$ of the crack with respect to the arrangement position of the sensor (distance from the reinforcement). As shown in these figures, FIG. 9 shows the case where the crack depth is 400 mm and the distance between the sensors $\Delta X$ is 30 mm, and FIG. 10 shows the case where the crack depth is 195 mm and the sensor distance $\Delta X$ is 5 mm. As shown in these Figures, the error in measurement is less than or equal to 5%. Thus, the crack depth can be measured at quite high precision.

It should be noted that the apparatus employing these crack measurement can be constructed with a pair of transmitting sensor and a receiving sensor, an arithmetic portion for performing analysis of the reception and an ultrasonic wave oscillator. Amongst, the arithmetic portion and a control portion controlling the ultrasonic wave oscillator and so forth are constructed by a personal computer or so forth. Namely, by providing an A/D converter port for inputting the detection signal of the reception wave from the reception sensor and a digital signal processor in the personal computer, and by connecting the ultrasonic wave oscillator with the ultrasonic wave transmitter and the ultrasonic wave receiving sensor, the apparatus can be realized. As the personal computer, portable type personal computer may be utilized. Therefore, the depth measurement of the crack can be quickly done in the site, and high precision measurement of the crack can be done easily.

On the other hand, in order to transmit and receive the ultrasonic wave at two positions, it is possible to provide two sets of the ultrasonic wave sensor units to arrange respective set of the sensor units in a spaced apart relationship so that crack depth may be measured by alternatively transmitting and receiving the ultrasonic wave between the sensors without shifting the sensor positions.

Another embodiment of the present invention will be discussed hereinafter with reference to the accompanying drawings.

Figure 15A:
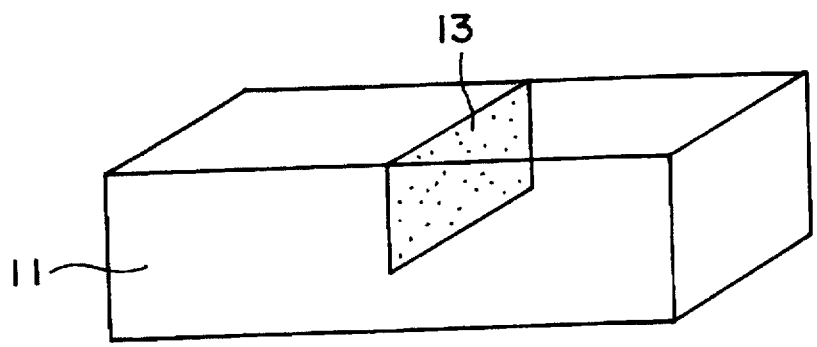
FIGS. 15A, 15B and 15C are diagrammatic illustrations showing a concrete model for verifying the effect of the invention.
Figure 15B:
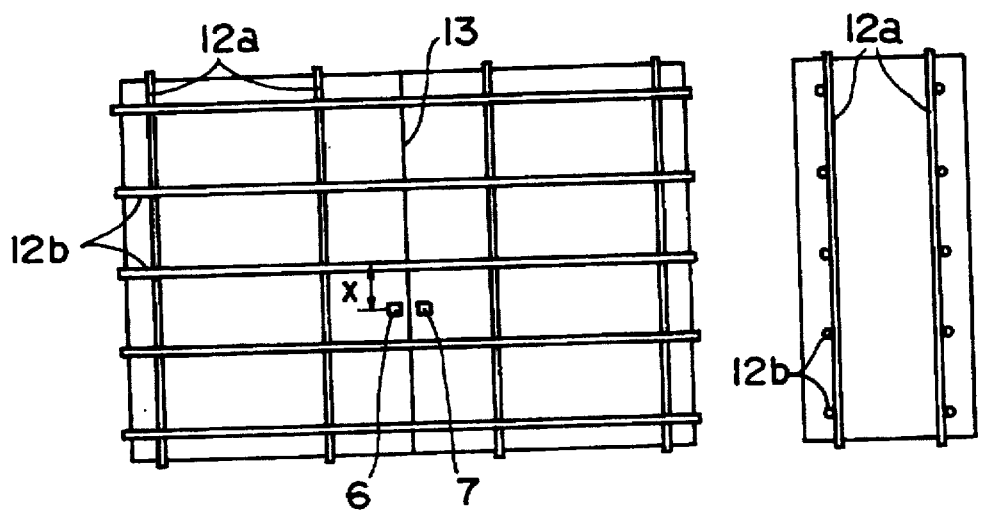

FIG. 15A is a diagrammatic illustration showing a reinforced concrete model utilized in the analysis. As shown in FIG. 15A, the concrete block 11 is in a form of rectangular parallelpiped configuration having dimension of 1000 mm×300 mm×700 mm. The concrete block 11 has a crack 13 in a size of 700 mm in length and 195 mm in depth on the surface of 1000 mm×700 mm in parallel to the surface of 300 mm×700 mm. On the other hand, as shown in FIG. 15B, within the concrete 11, 13 mm diameter of reinforcements 12a (distributing bar) are buried in parallel to the crack 13. The pitch of the reinforcements 12a is 300 mm in the direction perpendicular to the crack and 200 mm in the depth direction. Also, 16 mm diameter of reinforcements 12b (main reinforcement) is buried in the perpendicular to the crack. The distance between the reinforcements 12b is 150 mm in the direction parallel to the crack 13 and 200 mm in the depth direction. Among these reinforcements 12a and 12b, ones close to the surface of the concrete are located in the depth of 50 mm from the surface of the concrete. At the position which is away from the reinforcement 12b by x along the crack 13 of the concrete, the ultrasonic wave transmitting sensor 6 and the ultrasonic wave receiving sensor 7 are arranged in opposition across the crack 13. The ultrasonic wave transmitted from the ultrasonic wave transmitting sensor 6 is received by the ultrasonic wave receiving sensor 7 for analysis.

In the reinforced concrete model as set forth above, the reception wave at a measuring point where the ultrasonic wave transmitting sensor 6 and the ultrasonic wave receiving sensor 7 are placed immediately above the reinforcement is expressed by CX00, the reception waves respectively measured at measuring points shifted along the crack in a pitch of 5 mm are expressed respectively CX05, CX10, . . . , CX90. The obtained reception waves are transformed by Fourier transformation to obtain Fourier spectrum. FIGS. 11A, 12A, 13A, and 14A show the obtained reception waves CX05, CX10, . . . , CX90 and FIGS. 11B, 12B, 13B, and 14B show the Fourier spectrums among obtained reception waves. It should be noted that, in FIG. 12B, the dotted line shows the spectrum of the transmitted wave.

Figure 11A:
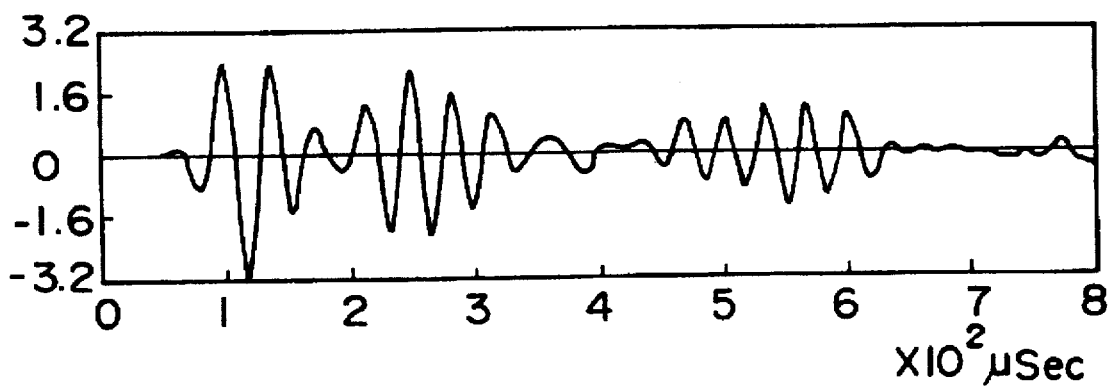
FIGS. 11A and 11B are graphs showing CX05 reception wave and a Fourier Spectrum of CX05 reception wave, respectively.
Figure 11B:
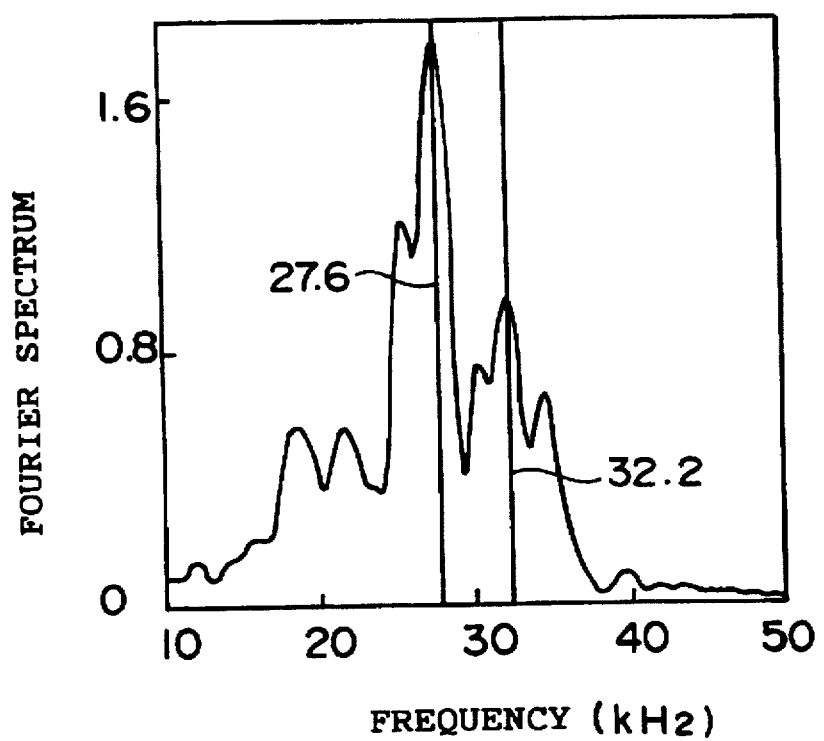
Figure 13A:
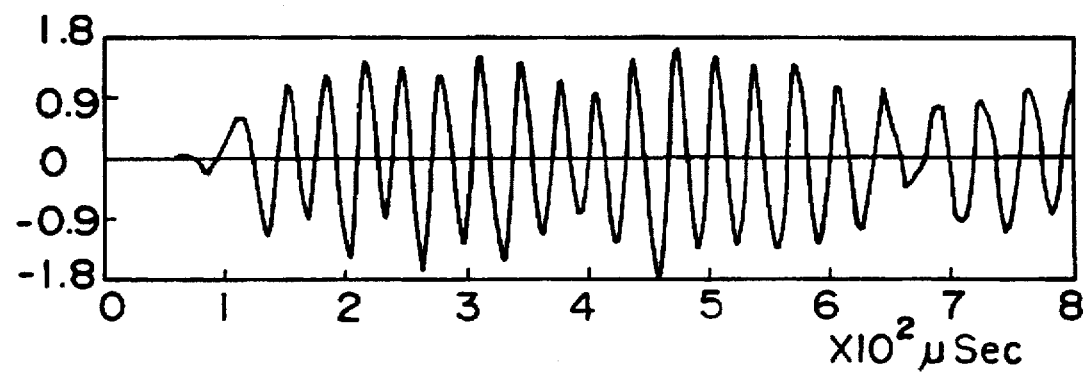
FIGS. 13A and 13B are graphs showing CX45 reception wave and a Fourier Spectrum of CX45 reception wave, respectively.
Figure 13B:
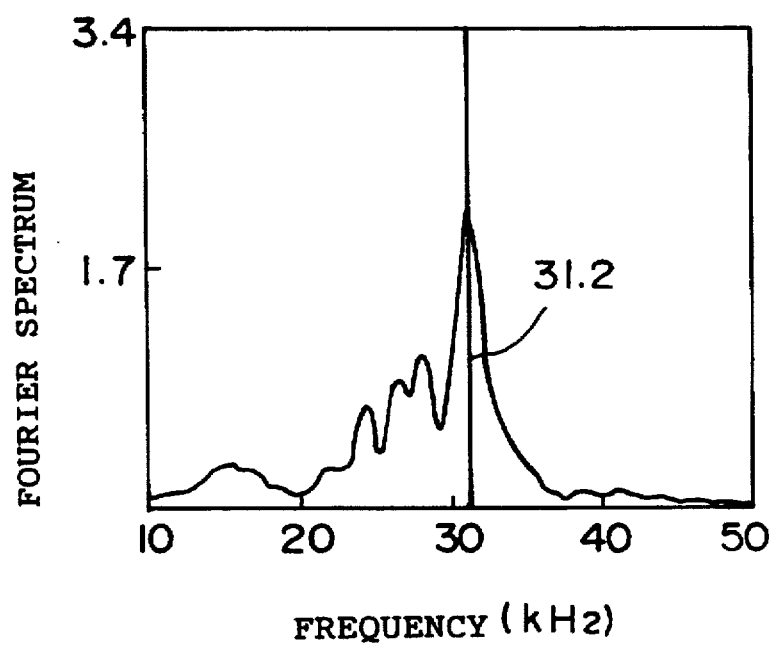
Figure 14A:
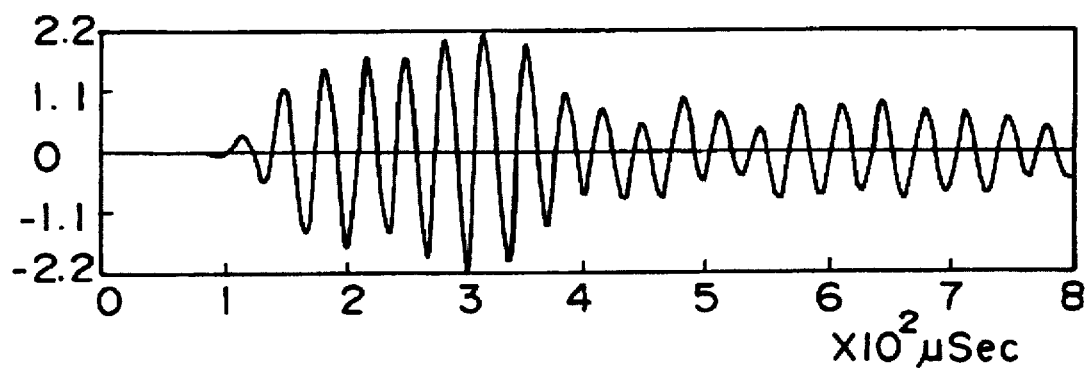
FIGS. 14A and 14B are graphs showing CX90 reception wave and a Fourier Spectrum of CX90 reception wave, respectively.
Figure 14B:
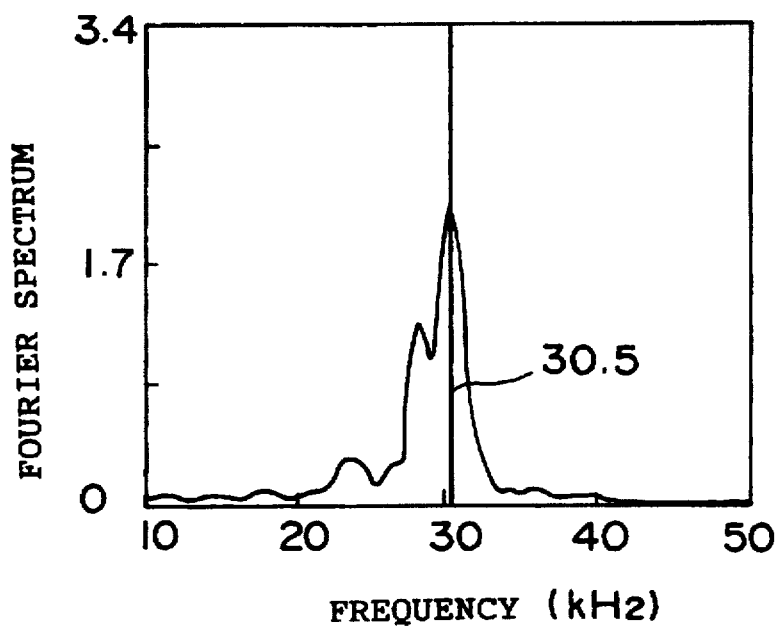

As shown in FIG. 11B, in the Fourier spectrum of CX05 measured at a point quite close to the reinforcement, i.e. 5 mm from the reinforcement in plan view, the peak having the highest intensity is present in the vicinity of 27 kHz. Next, higher peak is present in the vicinity of 32 kHz. On the other hand, as shown in FIG. 4B, in the Fourier spectrum of CX30 measured at the point distanced from the reinforcement in relatively small distance, i.e. 30 mm in the plan view, the high peak is present in the vicinity of 27 kHz similarly to the case of CX05. However, the relative intensity relative to the peak present in the vicinity of 30 kHz is smaller in comparison with the case of CX05. Also, as shown in FIGS. 13B and 14B, in the Fourier spectrums of CX45 distant from the reinforcement in relatively large distance, i.e. 45 mm in plan view, and of CX90 distant from the reinforcement in the significant distance, i.e. 90 mm in the plan view, the peaks present in the vicinity of 30 kHz are the highest, and the peaks in the vicinity of the 27 kHz are significantly lowered in comparison with the same of CX05 and CX30.

As set forth above, only spectrum in the vicinity of 30 kHz is held substantially unchanged in the peak values and the oscillation frequency even by shifting the measuring point. On the other hand, other spectrums, the dominant frequency and spectrum value are varied significantly, namely, according to shifting of the measuring point away from the position immediately above the reinforcement, the spectrum in the vicinity of 30 kHz becomes remarkable.

Figure 12A:
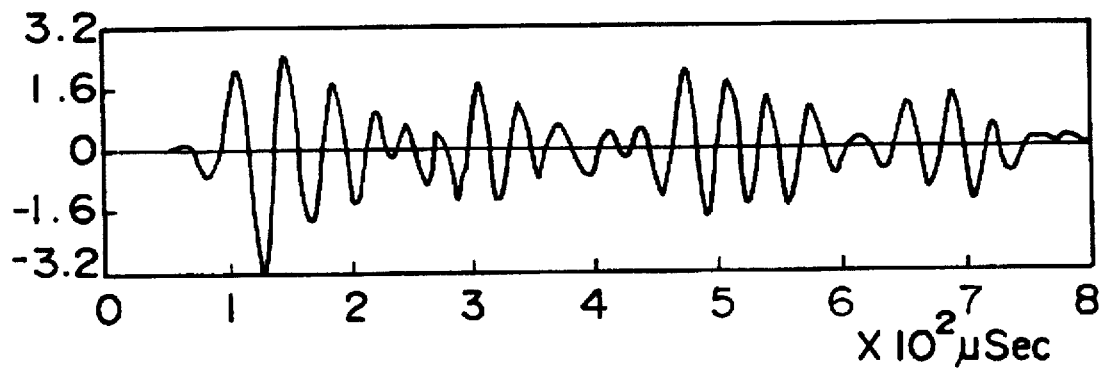
FIGS. 12A and 12B are graphs showing CX30 reception wave and a Fourier Spectrum of CX30 reception wave, respectively.
Figure 12B:
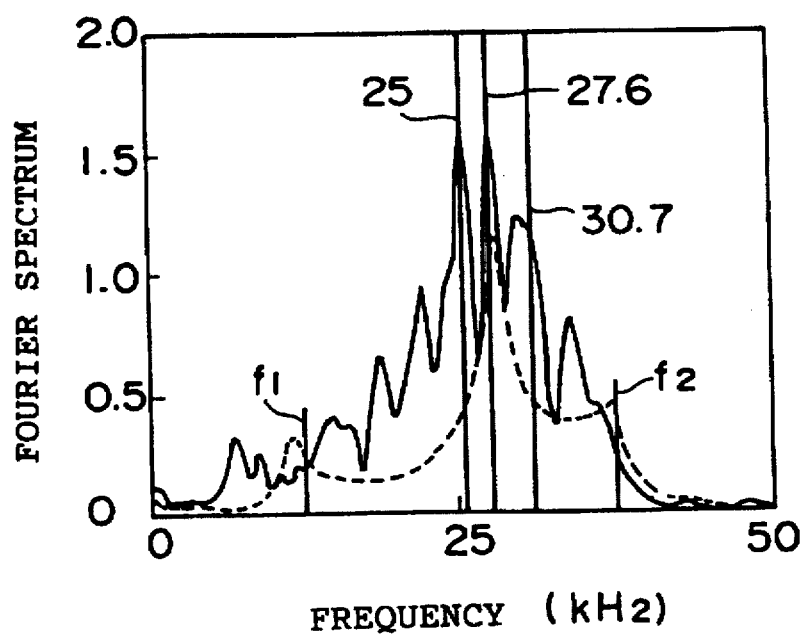

Therefore, as shown in FIG. 12b, when the spectrum of 30.7 kHz can be extracted among the spectrums in the vicinity of the predominant oscillation frequency of the transmitted wave, and by performing inverse Fourier transformation for such spectrum, a time sequence wave of the ultrasonic wave reflected by the bottom of the crack can be reproduced. Then, by replacing the item in the first mentioned equation (1) with a time $t_h$ required for receiving the time sequence wave by the reception sensor, the depth d of the crack can be obtained.

Therefore, the inventors have found as a results of various experiments and study, to perform converging calculation. At first, with respect to the Fourier spectrum of the reception wave, the arbitrary frequency range less than or equal to $f_1$ and higher than or equal to $f_2$ are cut off, as shown in FIG. 12B. For the obtained spectrum, inverse Fourier transformation is performed to generate the time sequence wave. Next, the Fourier spectrum of the generated time sequence wave is calculated. From the Fourier spectrum, the frequency range lower than or equal to $(f_1+\Delta f_1)$ is cut off, and further, the frequency range higher than or equal to $(f_2-\Delta f_2)$ is cut off to generate another time sequence wave. Then the Fourier spectrum of the generated another time sequence wave is calculated. From the Fourier spectrum, the frequency range lower than or equal to $(f_1+2\Delta f_1)$ is cut off, and further, the frequency range higher than or equal to $(f_2-2\Delta f_2)$ is cut off to generate another time sequence wave. As set forth above, by repeating the foregoing calculation, the rising timing of the time sequence wave finally obtained and replaced in the foregoing equation (1) to derive the depth of the crack.

When the crack depth is derived by the foregoing converging calculation, it is possible that the converging calculation is outbroken so as not to obtain the solution. However, even in such case, by providing a time sequence filter for the superimposed reception wave and thus preparing the wave form where the amplitude of wave of the rising portion of the reflected wave form the reinforcement, the converging calculation can be performed stably so that the crack depth can be derived with high precision.

Next, discussion will be given with respect to the result of actual measurement of the rising timing of the wave from the bottom of the crack by utilizing the fact that the dominant frequencies are slightly differentiated between the wave from the reinforcement, the wave from the bottom of the crack and the wave from other route (for example reflection from the bottom surface of the concrete), and by removing or eliminating the wave from the reinforcement. In the model of FIG. 15A, the reception signal obtained by arranging the sensors immediately above the reinforcement is assumed as C00, the reception wave obtained through transmission and reception of the ultrasonic wave by the sensors located at the position shifted way from the position immediately above the reinforcement for 10 mm is assumed as C10, the reception wave obtained through transmission and reception of the ultrasonic wave by the sensors located at the position shifted way from the position immediately above the reinforcement for 30 mm is assumed as C30.

Figure 16:
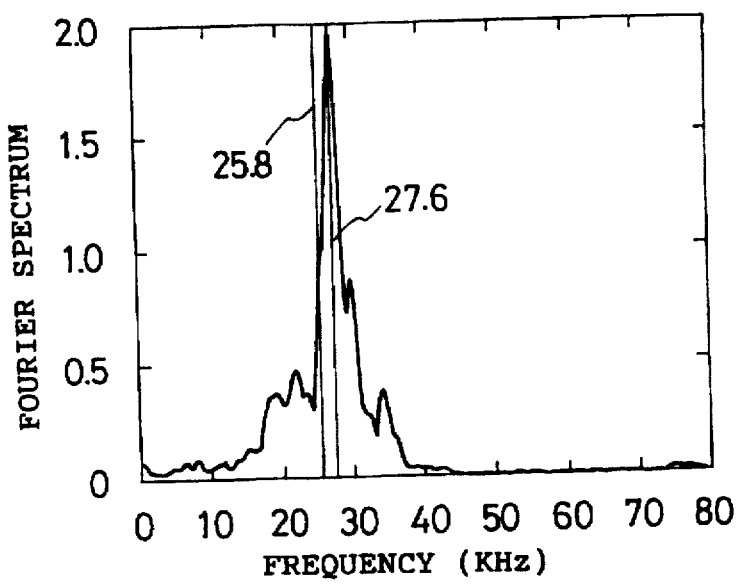
FIG. 16 is a graph showing a Fourier spectrum of C00 reception wave.

FIG. 16 shows the Fourier spectrum of C00. For this spectrum, $f_1=24$ kHz, $f_2=37$ kHz, and $\Delta f_1=500$ Hz, and $\Delta f_2=50$ Hz are applied to perform converging calculation.

Figure 17A:
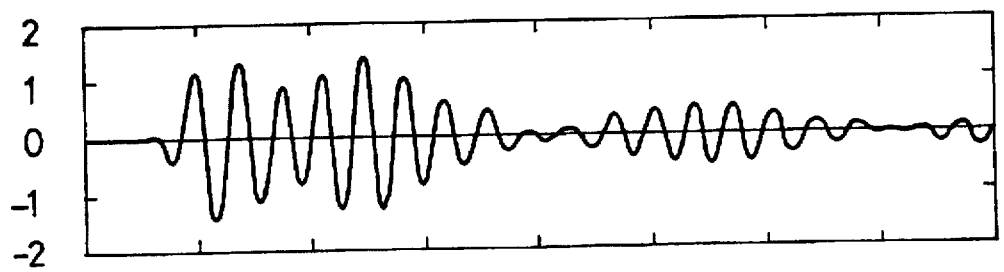
FIGS. 17A and 17B are graphs showing the original wave and the converging wave of a C00 reception wave, respectively.
Figure 17B:
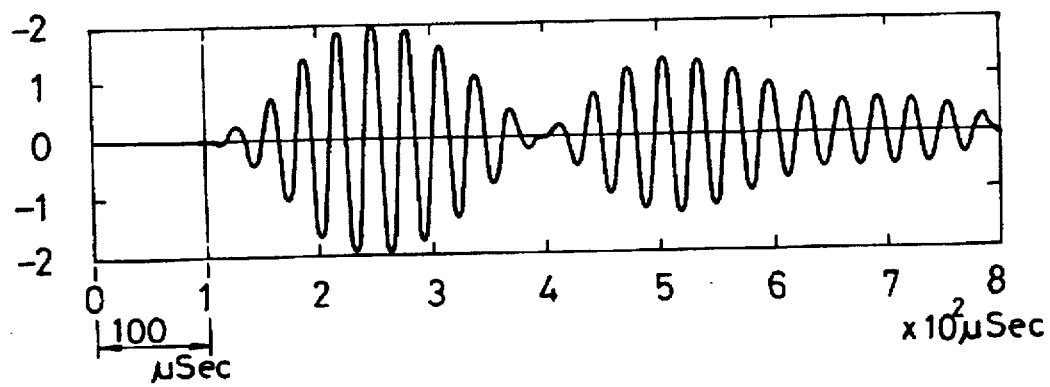
Figure 18A:
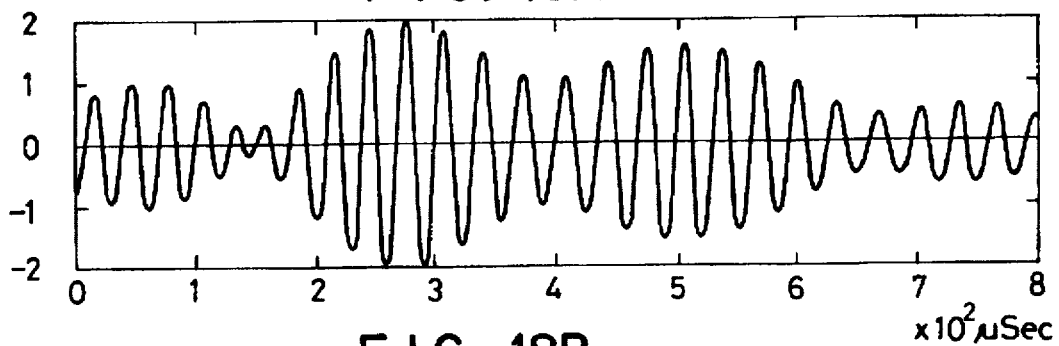
FIGS. 18A to 18D are graphs showing a manner of converging of the C00 reception wave.
Figure 18B:
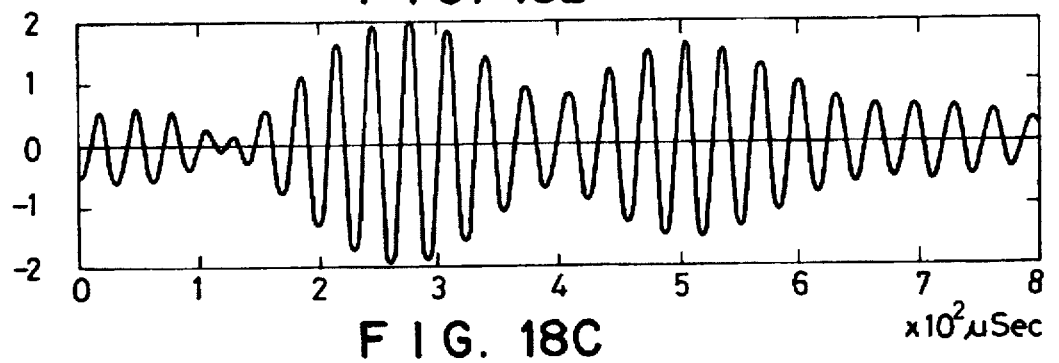
Figure 18C:
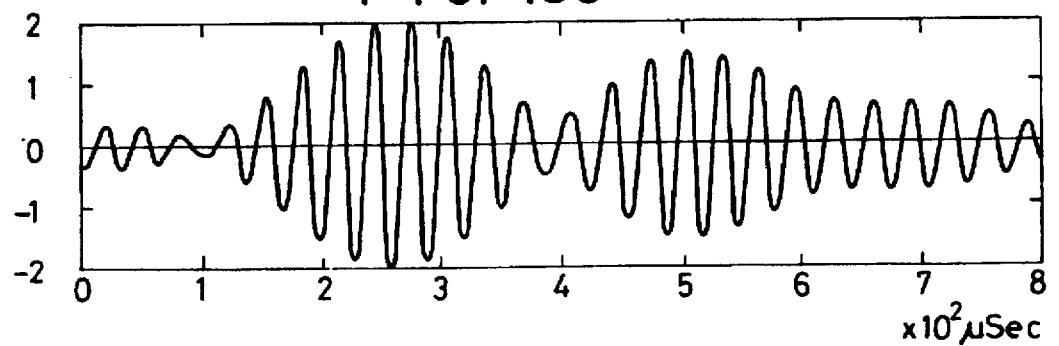
Figure 18D:
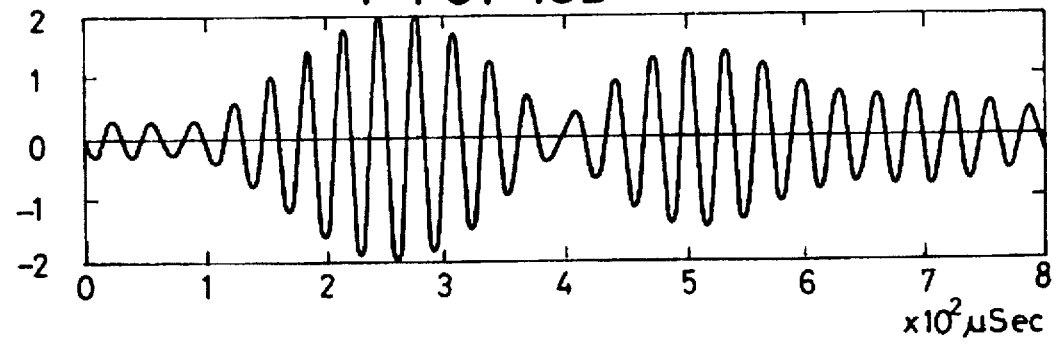

The original wave of C00 is shown in FIG. 17A and the converged wave form is shown in FIG. 17B. FIGS. 18A, 18B, 18C, and 18D shows the process of convergence. In the converged waveform of FIGS. 18A, 18B, 18C, and 18D, a standing wave is superimposed during convergence. Therefore, by removing the standing wave and comparing with the original wave of C00, the converged waveform is obtained. In this case, the rising time of the wave reflected from the deepest portion of the crack becomes t=100 μsec. Then, the depth d of the crack is derived through the following equation utilizing the sonic speed of the concrete of 3.88 mm/μsec, which is obtained through experiments.

$$d=3.88\times100/2=194 \text{ mm} \tag{3}$$

The crack depth obtained from the calculation set forth above is substantially matched with the actual crack depth, i.e. 195 mm with an error of 0.5%.

Figure 19:
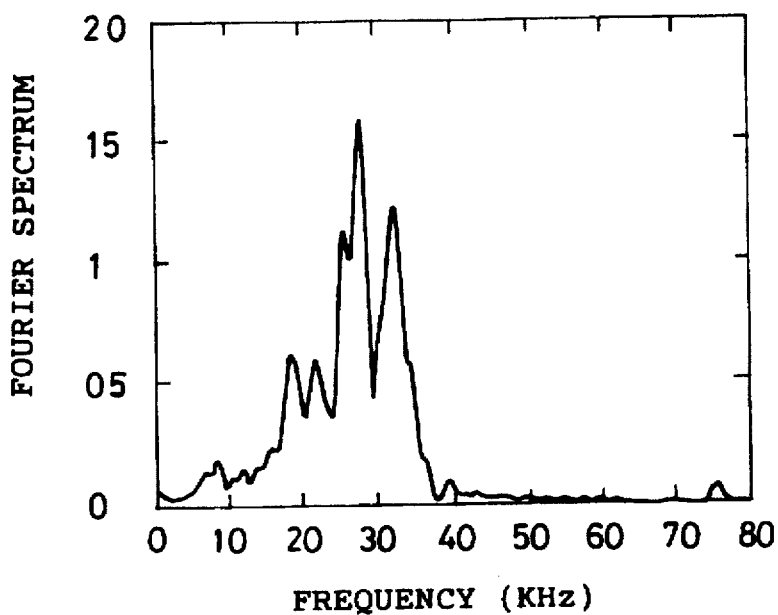
FIG. 19 is a graph showing a Fourier spectrum of C10 reception wave.
Figure 20A:
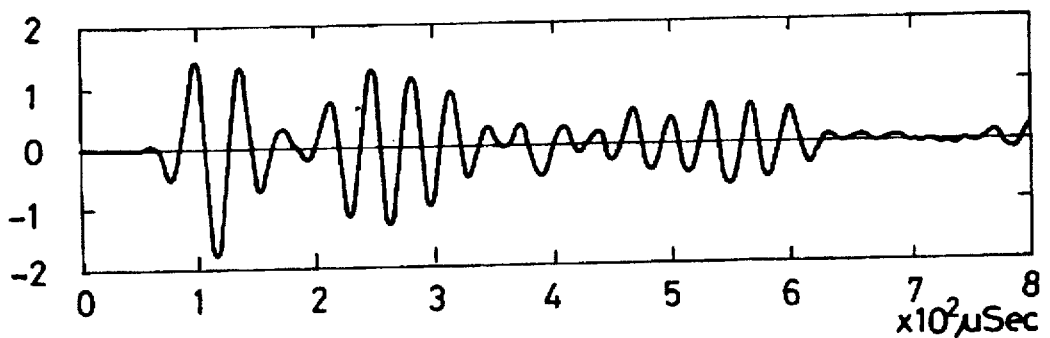
FIGS. 20A and 20B are graphs showing the original wave and the converging wave of a C10 reception wave, respectively.
Figure 20B:
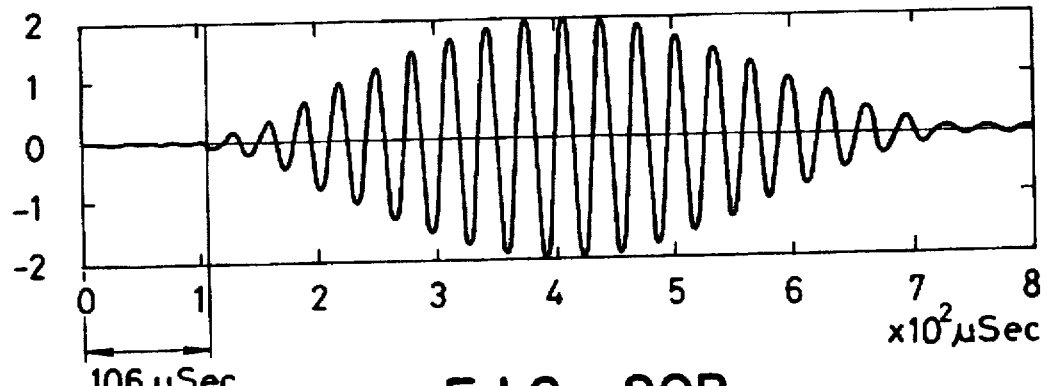
Figure 21A:
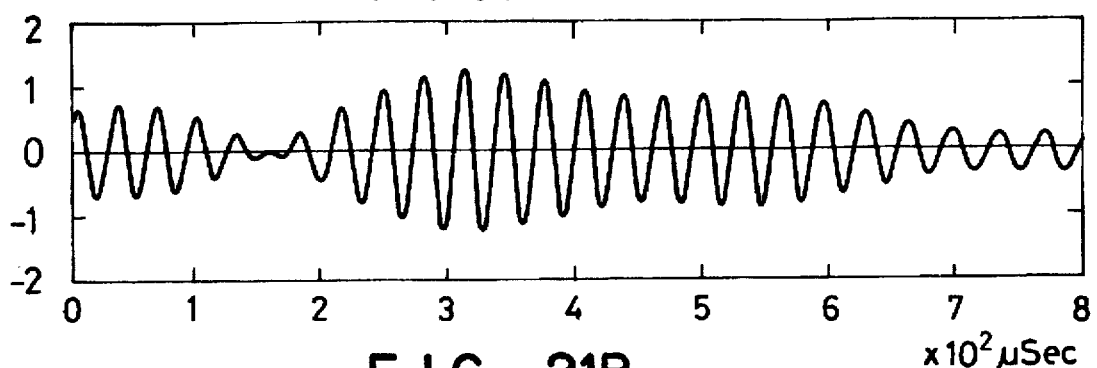
FIGS. 21A to 21D are graphs showing a manner of converging of the C10 reception wave.
Figure 21B:
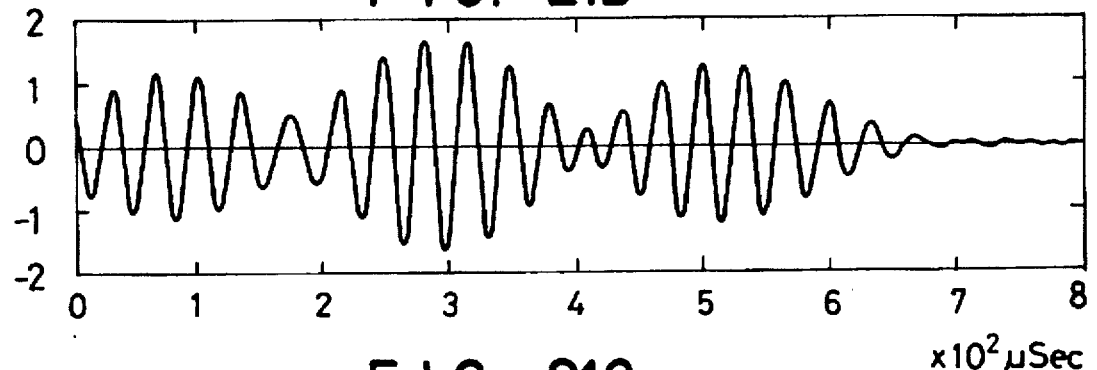
Figure 21C:
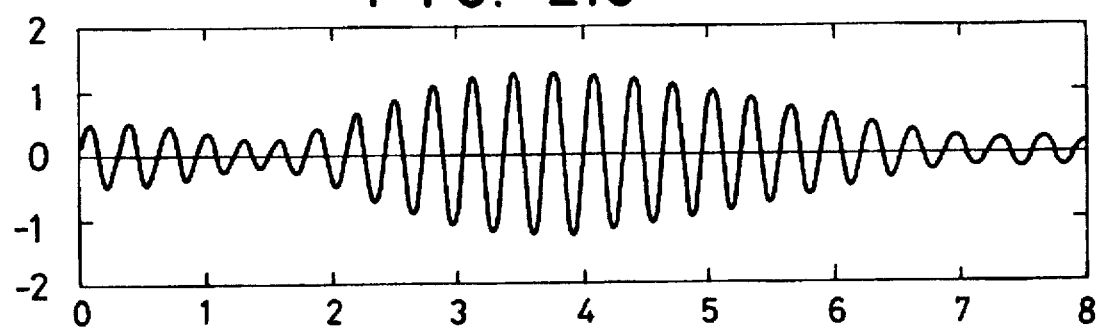
Figure 21D:
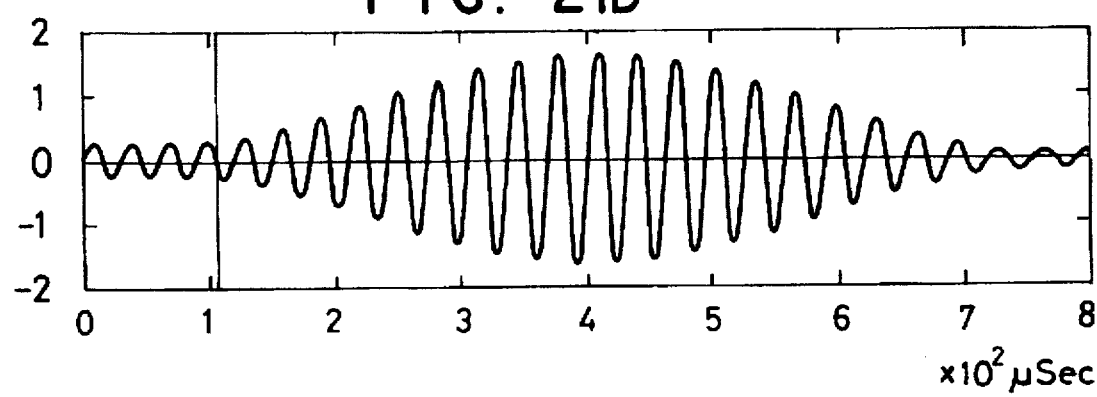
Figure 24A:
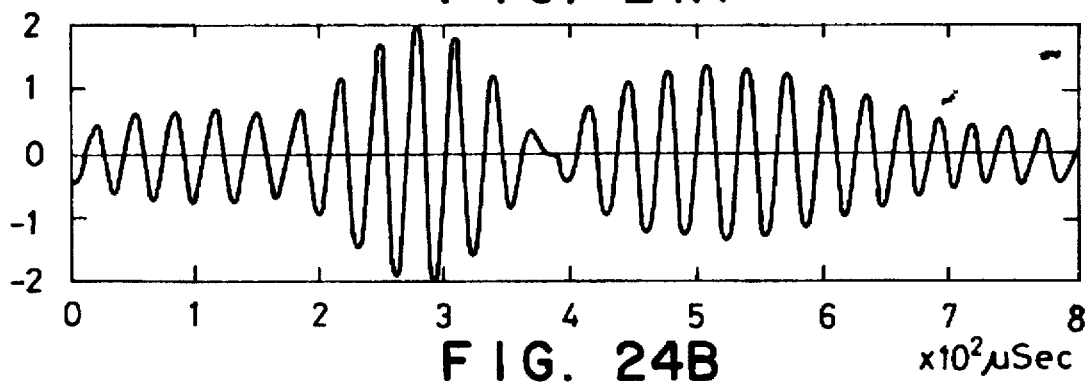
FIGS. 24A to 24D are graphs showing a manner of converging of the C30 reception wave.
Figure 24B:
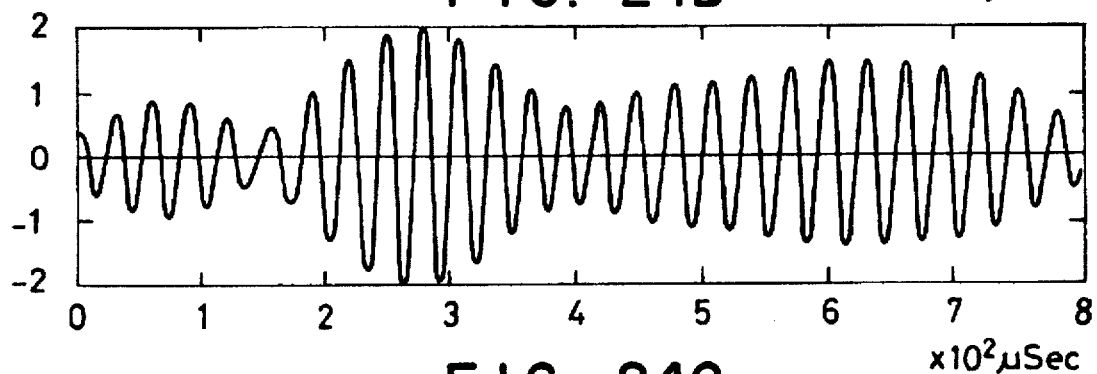
Figure 24C:
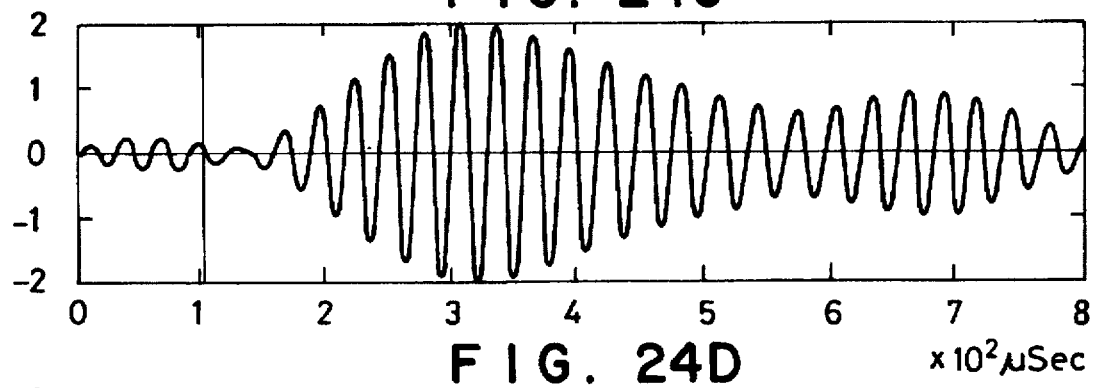
Figure 24D:
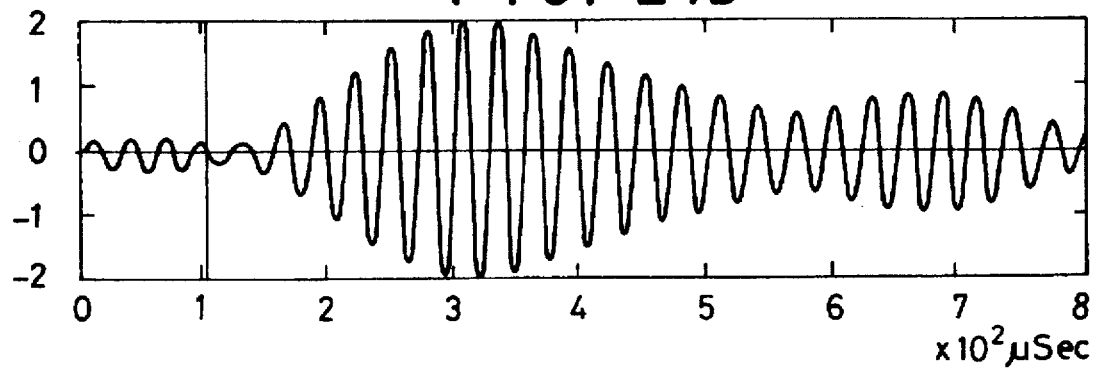

Next, discussion will be given for the result of convergence with respect to the wave of C10. FIG. 19 shows the Fourier spectrum of the C10 wave. The process of converging calculation by applying $f_1=24$ kHz, $f_1=35$ kHz, $\Delta f_1=500$ Hz and $\Delta f_1=100$ Hz for the spectrum is shown in FIGS. 21A, 21B, 21C, and 21D. Also, the original wave is shown in FIG. 20A, and the converged wave removed the standing wave is shown in FIG. 20B. In this case, the crack depth d becomes 3.88×106/2=205.6 mm. Thus the error was 5.4%.

FIG. 22 shows the Fourier spectrum of wave C30. The process of converging calculation by applying $f_1=24$ kHz, $f_2=40$ kHz, $\Delta f_1=500$ Hz and $\Delta f_1=100$ Hz for the spectrum of the C30 wave is shown in FIG. 24A, 24B, 24C, and 24D. Also, the original wave is shown in FIG. 23A, and the converged wave removed the standing wave is shown in FIG. 23B. In this case, the crack depth d becomes 3.88× 105/2=203.7 mm. Thus the error was 4.5%.

Similarly, in the model shown in FIG. 15A, the measured value of the depth of the crack in the case where the sensor is placed other positions. In the model shown in FIG. 25, the discussion will be given for the result of measurement of the depth of the crack by locating the sensor at various positions.

The following table 1 is the result of measurement.

| Filter | $f_1$ (KHz) | $f_2$ (KHz) | $\Delta f_1$ (Hz) | $\Delta f_2$ (Hz) | Converging Condition | Rise Time (μsec) |
|---|---|---|---|---|---|---|
| C00 | NO | 24 | 37 | 500 | 50 | ○ | 100 μsec |
| C10 | NO | 24 | 35 | 500 | 100 | ○ | 106 |
| C30 | NO | 24 | 40 | 500 | 0 | ○ | 105 |
| C40 | NO | 24 | 38 | 500 | 0 | ○ | 100 |
| C50 | NO | 24 | 38 | 500 | 0 | ○ | 100 |
| C70 | NO | 24 | 38 | 500 | 0 | ○ | 100 |
| B00 | NO | 24 | 38 | 30 | 50 | X | outbreak |
| B30 | NO | 24 | 38 | 30 | 50 | X | outbreak |
| B60 | NO | 24 | 38 | 30 | 50 | X | outbreak |
| B100 | NO | 24 | 38 | 30 | 50 | Δ | 200 |
| B125 | NO | 24 | 38 | 30 | 50 | X | outbreak |

-continued

| Filter | $f_1$ (KHz) | $f_2$ (KHz) | $\Delta f_1$ (Hz) | $\Delta f_2$ (Hz) | Converging Condition | Rise Time (μsec) |
|---|---|---|---|---|---|---|
| B145 NO | 24 | 38 | 30 | 50 | △ | outbreak |
| B00 YES | 24 | 38 | 500 | 0 | ⊚ | 190 |
| B30 YES | 24 | 38 | 500 | 0 | ⊚ | 190 |
| B60 YES | 24 | 38 | 500 | 0 | ⊚ | 200 |
| B100 YES | 24 | 38 | 500 | 0 | ⊚ | 200 |
| B125 YES | 24 | 38 | 500 | 0 | ⊚ | 200 |
| B145 YES | 24 | 38 | 500 | 0 | ⊚ | 200 |

Figure 25:
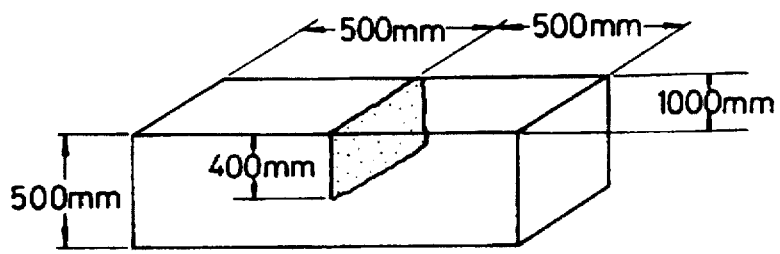
FIG. 25 is a diagrammatic illustration showing another concrete model for demonstrating the effect of the invention.

It should be noted, for example B60 means that, in the model of FIG. 25, the distance between the reinforcement and the sensor in the plan view is 60 mm.

Figure 15C:
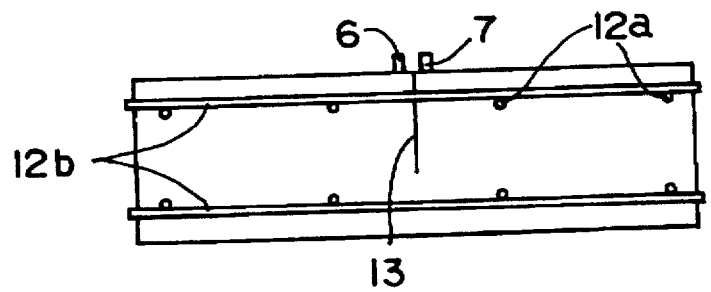

As can be seen from the foregoing table 1, while the convergence is achieved in the model of FIG. 15, despite of convergence calculation with $\Delta f_1=30$ Hz and $\Delta f_2=50$ Hz, solution was outbroken in the case of model of FIG. 25.

Figure 26A:
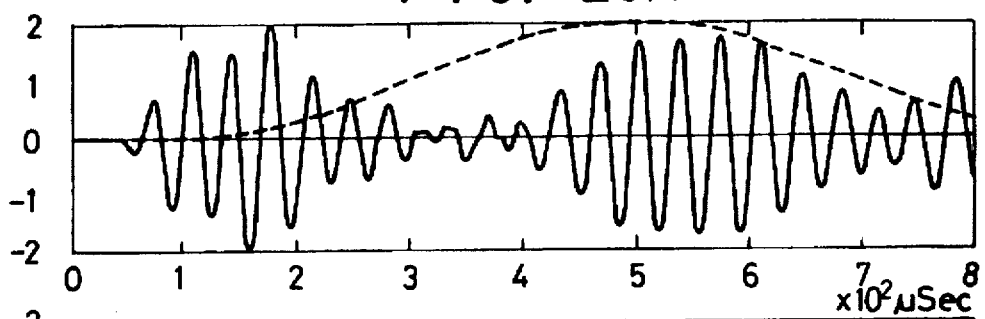
FIGS. 26A, 26B and 26C are graphs showing converging condition by filtering in the model of FIG. 25.
Figure 26B:
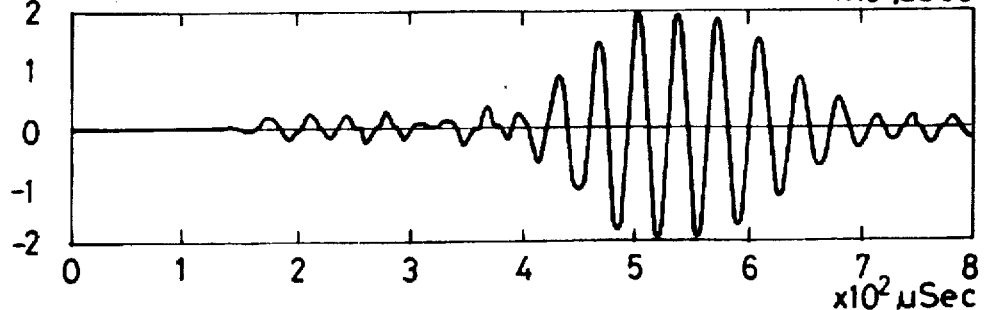
Figure 26C:
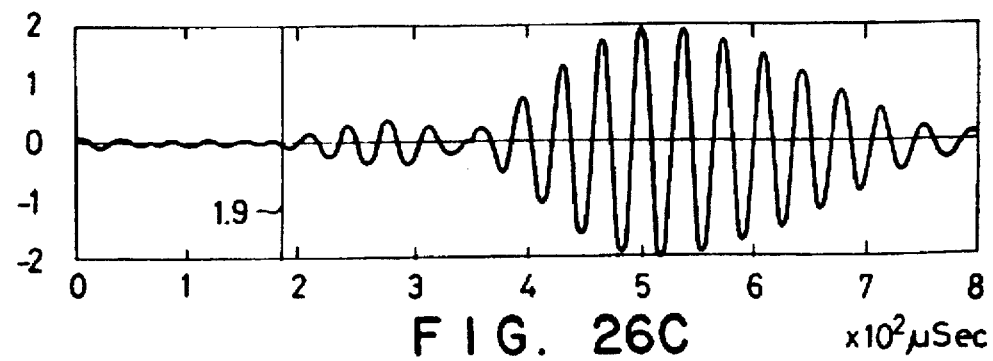

When the solution is outbroken, it becomes possible to achieve convergence by filtering process of the time sequence wave. FIG. 26A shows the time sequence wave of the reception wave, in which a filter (period 800 μsec.) having characteristics as illustrated by the broken line is provided to forcedly lower the amplitude in rising of the wave reflected from the reinforcement. Thus, the waveform after filtering becomes as shown in FIG. 26B. When convergence is performing with respect to such filtered time sequence wave, rising timing of the wave from the crack can be obtained as shown in FIG. 26C. As shown in the foregoing table 1 m the rising time of the wave from the crack was in a range of 190 μsec to 200 μsec. The crack depth d derived from such rising time are in a range of 368 mm to 388 mm. Since the actual depth of the crack is 400 mm, it can be said that quite close values could be obtained. It should be noted that the frequency of the filter is not specified to the range employed in the shown embodiment.

Thus, by performing converging calculation utilizing Fourier transformation and inverse Fourier transformation, the rise time of the wave from the crack can be obtained. Therefore, the depth d of the crack can be precisely obtained. Also, when the converging calculation causes outbreak, the depth d of the crack can be obtained by filtering process.

It should be noted that the apparatus to be employed for measurement of crack can be constructed with a pair of transmitting sensor and a receiving sensor, an arithmetic portion for performing analysis of the reception and an ultrasonic wave oscillator. Amongst, the arithmetic portion and a control portion controlling the ultrasonic wave oscillator and so forth are constructed by a personal computer or so forth. Namely, by providing an A/D converter port for inputting the detection signal of the reception wave from the reception sensor and a digital signal processor in the personal computer, and by connecting the ultrasonic wave oscillator with the ultrasonic wave transmitter and the ultrasonic wave receiving sensor, the apparatus can be realized. As the personal computer, portable type personal computer may be utilized. Therefore, the depth measurement of the crack can be quickly done in the site, and high precision measurement of the crack can be done easily.

Although the invention has been illustrated and described with respect to exemplary embodiment thereof, it should be understood by those skilled in the art that the foregoing and various other changes, omissions and additions may be made therein and thereto, without departing from the spirit and scope of the present invention. Therefore, the present invention should not be understood as limited to the specific embodiment set out above but to include all possible embodiments which can be embodies within a scope encompassed and equivalents thereof with respect to the feature set out in the appended claims.

What is claimed is:

1. A method for measuring a depth of a crack in a reinforced concrete construction, comprising the steps of:

providing an ultrasonic wave transmitting sensor and an ultrasonic wave receiving sensor in opposition across a crack at a first position;

transmitting an ultrasonic wave by said ultrasonic wave transmitting sensor at said first position;

receiving a reflected ultrasonic wave by said ultrasonic wave receiving sensor at said first position;

positioning said ultrasonic wave transmitting sensor and said ultrasonic wave receiving sensor at a second position distanced from said first position along the crack;

transmitting an ultrasonic wave from said ultrasonic wave transmitting portion at said second position;

receiving a reflected ultrasonic wave by said ultrasonic wave receiving sensor at said second position;

determining a mutual phase shift $\Delta t$ between the received wave at said first position and the received wave at said second position;

phase shifting the received waves such that components of the received waves representing secondary reflections are in reversed phases;

summing the phase shifted received waves to cancel the components representing secondary reflections and thereby detect a rise time of a wave reflected from said crack; and deriving a depth of the crack based on said rise time.

2. A method for measuring a depth of a crack in a reinforced concrete construction, comprising the steps of:

providing at least two pairs of an ultrasonic wave transmitting sensor and a corresponding ultrasonic wave receiving sensor at said reinforced concrete construction at different positions, each pair being provided in opposition across a crack;

transmitting an incident ultrasonic wave by each said ultrasonic wave transmitting sensor;

receiving a reflected ultrasonic wave of said incident ultrasonic wave by each said corresponding ultrasonic wave receiving sensor;

determining a mutual phase shift $\Delta t$ between each received reflected ultrasonic wave;

phase shifting the received waves such that components of the received waves representing secondary reflections are in reversed phases;

summing the phase shifted received waves to cancel out the components of the received waves representing secondary reflections and to detect a rise time of a wave reflected from said crack; and deriving a depth of the crack based on said rise time.

3. A crack depth measuring apparatus comprising:

at least one pair of an ultrasonic wave transmitting sensor which transmits an incident ultrasonic wave and an ultrasonic wave receiving sensor which receives a reflected ultrasonic wave of said incident ultrasonic wave at different positions; and an arithmetic unit which determines a mutual phase shift $\Delta t$ between waves received by each said ultrasonic wave receiving sensor of said at least one pair of an ultrasonic wave transmitting sensor and ultrasonic wave receiving sensor at different positions and phase shifts the received waves such that components of each wave representing secondary reflections are in reversed phase and sums the phase shifted received waves to cancel out the components of each wave representing secondary reflections and to detect a rise time of a component of each reflected ultrasonic wave reflected from said crack and derive a depth of the crack based on said rise time.

4. A method for measuring a depth of a crack in a reinforced concrete construction, comprising the steps of:

providing an ultrasonic wave transmitting sensor and a corresponding ultrasonic wave receiving sensor in opposition across a crack;

transmitting an ultrasonic wave by said ultrasonic wave transmitting sensor and receiving a reflected ultrasonic wave by said corresponding ultrasonic wave receiving sensor;

performing a Fourier transformation on the received wave to produce a Fourier spectrum;

selecting a predetermined frequency range of the Fourier spectrum;

performing an inverse Fourier transformation on the predetermined frequency range of the Fourier spectrum to reconstruct the received wave;

repeating said performing a Fourier transformation step, said selecting a predetermined frequency range step and said performing an inverse Fourier transformation step until convergence is obtained on a rise time of a component of the received wave comprising a reflection from said crack and deriving a depth of the crack based on said rise time.

5. A crack depth measuring method as set forth in claim 4, wherein a filter having a sine curve characteristics is applied to said received wave.

6. A crack depth measuring apparatus comprising:

at least an ultrasonic wave transmitting sensor which transmits an ultrasonic wave;

at least one respective ultrasonic wave receiving sensor placed in opposition across a crack to said ultrasonic wave transmitting sensor; and a signal processing portion repeatedly effecting a Fourier transformation on a wave received by said ultrasonic wave receiving sensor and selecting a predetermined frequency range from the Fourier transformation and effecting inverse Fourier transformation on the predetermined frequency of the Fourier transformation until convergence is obtained on a rise time of a component of the received wave comprising a reflection from said crack and deriving a depth of the crack based on said rise time.

7. A method for measuring a depth of a crack in a reinforced concrete construction, comprising the steps of:

providing an ultrasonic wave transmitting sensor and an ultrasonic wave receiving sensor in opposition across a crack at a first position;

transmitting an ultrasonic wave by said ultrasonic wave transmitting sensor at said first position;

receiving a reflected ultrasonic wave by said ultrasonic wave receiving sensor at said first position;

positioning said ultrasonic wave transmitting sensor and said ultrasonic wave receiving sensor at a second position distanced from said first position along the crack;

transmitting an ultrasonic wave from said ultrasonic wave transmitting portion at said second position;

receiving a reflected ultrasonic wave by said ultrasonic wave receiving sensor at said second position;

performing Fourier transformations on the wave received at said first position and on the wave received at said second position to obtain a Fourier spectrum for each wave;

selecting a frequency range based on the amplitude of the Fourier spectrum for each wave within the frequency range selected being substantially unchanged;

performing an inverse Fourier transformation in the frequency range selected on each received wave and thereby obtain a time sequence component representing a reflection from said crack;

determining a rise time of the time sequence component representing a reflection from said crack; and deriving a depth of the crack based on said rise time.

* * * * *

UNITED STATES PATENT AND TRADEMARK OFFICE
CERTIFICATE OF CORRECTION

PATENT NO. : 5,675,085
DATED : October 7, 1997
INVENTOR(S) : Masao HAYASHI, et al.

It is certified that error appears in the above-identified patent and that said Letters Patent is hereby corrected as shown below:

On the title page, item [75], the first Inventor's name should be:

--Masao HAYASHI--

Signed and Sealed this

Sixteenth Day of December, 1997

Attest:

BRUCE LEHMAN

Attesting Officer

Commissioner of Patents and Trademarks